United States Patent
Kilway et al.

(10) Patent No.: US 9,186,302 B2
(45) Date of Patent: Nov. 17, 2015

(54) BIOMATERIAL COMPOSITIONS

(75) Inventors: Kathleen V. Kilway, Kansas City, MO (US); Lynda F. Bonewald, Kansas City, KS (US); Thomas P. Schuman, Rolla, MO (US)

(73) Assignee: CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 13/880,783

(22) PCT Filed: Oct. 28, 2011

(86) PCT No.: PCT/US2011/058381
§ 371 (c)(1),
(2), (4) Date: Apr. 22, 2013

(87) PCT Pub. No.: WO2012/058591
PCT Pub. Date: May 3, 2012

(65) Prior Publication Data
US 2013/0210953 A1    Aug. 15, 2013

Related U.S. Application Data

(60) Provisional application No. 61/456,045, filed on Oct. 29, 2010.

(51) Int. Cl.
| | |
|---|---|
| *A61K 6/093* | (2006.01) |
| *A61K 6/00* | (2006.01) |
| *A61L 24/04* | (2006.01) |
| *A61L 27/18* | (2006.01) |
| *C08F 2/50* | (2006.01) |
| *C08G 77/60* | (2006.01) |

(52) U.S. Cl.
CPC ............ *A61K 6/093* (2013.01); *A61K 6/0052* (2013.01); *A61K 6/0067* (2013.01); *A61L 24/046* (2013.01); *A61L 27/18* (2013.01); *C08F 2/50* (2013.01); *C08G 77/60* (2013.01); *A61L 2430/02* (2013.01); *A61L 2430/06* (2013.01); *A61L 2430/12* (2013.01); *A61L 2430/24* (2013.01)

(58) Field of Classification Search
CPC ..... A61K 6/0052; A61K 6/093; C07F 7/0814
USPC ............................................ 522/170; 528/27
See application file for complete search history.

(56) References Cited

U.S. PATENT DOCUMENTS

| | | | |
|---|---|---|---|
| 5,169,962 A | 12/1992 | Crivello et al. | |
| 6,652,281 B1 | 11/2003 | Eckhardt et al. | |
| 2007/0072954 A1* | 3/2007 | Chappelow et al. | ............. 522/6 |
| 2008/0300340 A1 | 12/2008 | Gross et al. | |

FOREIGN PATENT DOCUMENTS

| | | | |
|---|---|---|---|
| WO | 2009 151957 | * | 12/2009 |
| WO | WO 2009/151957 | | 12/2009 |

OTHER PUBLICATIONS

International Search Report/Written Opinion dated Mar. 26, 2012 for co-pending PCT Application No. PCT/US2011/058381 filed on Oct. 28, 2011.

* cited by examiner

*Primary Examiner* — Kuo-Liang Peng
(74) *Attorney, Agent, or Firm* — Stinson Leonard Street LLP

(57) ABSTRACT

Biomaterial compositions comprising organosilicon monomers (such as silorane monomers) and chemical curing systems or dual chemical/light curing systems, in conjunction with optional tetraoxaspiro[5.5]undecanes ("TOSUs") and/or fillers. The present invention is directed to biomaterial compositions, as well as methods for manufacturing the same, and methods of using the compositions. The biomaterial composition comprises one or more organosilicon monomers (such as a silorane) and a chemical curing system or dual chemicaVlight curing system for polymerizing the 10 monomer(s). The compositions may include one or more tetraoxaspiro[5.5]undecanes "TOSUs") and/or fillers. Accelerators (such as photoacids), photosensitizers, and/or electron donors may also be included in the composition as appropriate.

31 Claims, 6 Drawing Sheets

US 9,186,302 B2

BIOMATERIAL COMPOSITIONS

CROSS-REFERENCE TO RELATED APPLICATIONS

This application is based on and claims priority to U.S. Non-Provisional Application Ser. No. 61/456,045 filed on Oct. 29, 2010, which is hereby incorporated herein by reference.

STATEMENT REGARDING FEDERALLY SPONSORED RESEARCH

This invention was made with government support under Department of Defense/USA Medical Research AQC Award No. W81XWH. The government has certain rights in the invention.

FIELD OF THE INVENTION

This invention relates in general to compositions of matter and more particularly, to compositions useful as biomaterials. The compositions comprise organosilicon monomers (preferably silorane monomers) and chemical curing systems or dual chemical/light curing systems. The compositions may include one or more tetraoxaspiro[5.5]undecanes ("TOSUs") and/or fillers. Photoacids, photosensitizers and/or a reaction promoters (electron donors) may also be included in the composition. The polymerizable compositions of the present invention are useful for a variety of applications, including use as biomaterials, for example as bone cements, bone stabilizers, dental composites, crowns, and the like.

DESCRIPTION OF RELATED ART

Bone fractures are suffered by nearly six million Americans each year. The common methods for fracture stabilization such as casts, splinting, intramedullary pinning, and external fixation, do have their drawbacks especially with regards to stabilization of small and growing bones. In addition to hampering soft tissue management, splinting cannot adequately stabilize highly unstable fractures or injuries with considerable bone loss. There must be sufficient bone cortex to support pin stabilization, especially with epiphyseal (near the end of the bone) fractures. These fractures lacking sufficient cortex often require pin placement across the adjacent joint leading to joint stiffness. Fractures in children can be further complicated by rapid growth of bone, thus requiring continual adjustment of the stabilization technique.

Frequently, bone cement has been used to stabilize fractures. The current bone cements are methacrylate based systems packaged in two components. The powder contains a mixture of polymethyl methacrylate ("PMMA"), methyl methacrylate-styrene-copolymer, and a radio opacifier (either barium sulfate or zirconium oxide). The second component is a liquid monomer typically containing methyl methacrylate, N,N-dimethyl-p-toluidine, and hydroquinone. The cure time of commercially available PMMA bone cements ranges from 6 to 22 minutes, and reaches a peak exotherm from 75 to 110° C. Thermal finite element models have found temperatures in excess of 60° C. at the bone cement and cancellous bone interface. The fracture toughness of bone cements generally ranges from 1.0 to 1.5 MPa/m$^2$. Flexural strength of bone cements ranges from 60 to 75 MPa and flexural modulus is between 2.2 and 3.3 GPa. Bone cements typically have a tensile strength of 50 to 60 MPa. These property values all meet or surpass the requirements described in ISO 5833 Implants for Surgery—Acrylic Resin Cements.

PMMA was first used in orthopedic surgery by Sir John Charnley for total hip arthroplasty in 1970 and the current formulation is essentially unchanged. Bone cement has different properties than other PMMA resins, due to both its additives and how it is prepared. Although the fully polymerized form of PMMA has good compatibility with human tissue, there are several drawbacks to its use. The monomer component is antigenic and induces severe toxicity, contraction with polymerization, and intense heat generation. These cements are highly exothermic, and have been shown to cause thermonecrosis in animal models. Bone cement typically has voids due to volatilization of the monomer during polymerization, which results in a porosity of 3 to 11%. Pressurization of the resin, as occurs during implantation of a femoral bone, can raise the boiling point of the monomer and decrease pore formation and size, but can be problematic if air is carried into the resin during implantation. The volume contracts by 5-7% during polymerization. This causes internal pores which can serve as crack initiators. The heat generated is determined by thickness/weight of resin, with a peak temperature rise in the range of 75-85° C. Although PMMA is biologically compatible, the monomer is an irritant and possible carcinogen. Unreacted residual monomer, approximately 3% after one hour, is present in the hardened polymer and can affect strength while leaching out into tissues, potentially causing hypotension, a common problem which can lead to possible cardiopulmonary events. The bone-resin interface is achieved by mechanical interlock, because the PMMA has no inherent adhesive properties. Dense bone causes less resin penetration, which can be an issue for resin fixation in younger patients such as military recruits whose bone structure may have less trabecular porosity. Use of bone cement in hip arthroplasties has also been shown to increase systematic levels of gamma-glutamytransperptidase ("GGTP"), which can result in anorexia and nausea/vomiting. Other drawbacks to the use of PMMA-based cements include lack of bioactivity, volumetric shrinkage upon polymerization, toxicity of the activator (N,N-dimethyl-p-toluidine) and possible involvement of the radiopacifier in third body wear. Therefore, it would be desirable to provide an alternative bone cement to PMMA-based cement.

BRIEF SUMMARY OF THE INVENTION

The present invention is directed to biomaterial compositions, as well as methods for manufacturing the same, and methods of using the compositions. The biomaterial composition comprises one or more organosilicon monomers (such as a silorane) and a chemical curing system or dual chemical/light curing system for polymerizing the monomer(s). The compositions may include one or more tetraoxaspiro[5.5] undecanes ("TOSUs") and/or fillers. Accelerators (such as photoacids), photosensitizers, and/or electron donors may also be included in the composition as appropriate.

The biomaterial compositions of the present invention are comparable to or superior to conventional PMMA systems in many characteristics. For example, in one aspect of the present invention, the compositions of the present invention exhibit significantly less polymerization stress without an associated proportional reduction in mechanical properties. In another aspect of the present invention, the biomaterial compositions exhibit enhanced biocompatibility and reduced cytotoxicity and genotoxicity. In general, the compositions of the present invention will not generate the cytotoxicity, antigenicity, polymerization stress, and heat generation that are characteristic of conventional PMMA bone cements.

In another aspect, it is anticipated that the biomaterial compositions of the present invention exhibit a peak exotherm below 50° C., more preferably below 45° C. For example, the silorane-based compositions of the present invention may exhibit a peak exotherm below about 49, 48, 47, 46, 45, 44, 43, 42, 40, 39, 38, 37, 36, 35, 33, 32, 31, or 30° C. Most preferably, the peak exotherm is within 1, 2, 3, 4, or 5° C. of the body temperature of the patient. For example, the P1 system (chemical curing system) and P2 systems (dual chemical/light curing system) described herein typically exhibit a peak exotherm of about 25 to 30° C. As such, it is anticipated that the biomaterial compositions of the present invention will not cause thermal necrosis.

The low exotherm of the chemically or dual cured silorane biomaterial (about 25- to 30° C.) compared to commercially available bone cement (about 70 to 90° C.) is an important property of the compositions of the present invention. Many antimicrobial agents and growth factors exhibit heat sensitivity. For example, proteins are degraded or denatured with increasing heat leading to inactivation or conversion to compounds with potential toxicity. Even antimicrobial agents such as silver (though relatively heat insensitive) may exhibit some heat sensitivity in certain crystalline forms. Importantly, conventional bone cements have not included growth factors (such as bone morphogenetic protein 2) due to their thermal instability. See Prountos et al., *The effect of antibiotics on bone healing: current evidence*, Expert Opin Drug Saf. 10 935-945 (2011); Yano et al., *Osteoinductive capacity and heat stability of recombinant human bone morphogenetic protein-2 produced by Escherichia coli and dimerlized by biochemical processing*, J Bone Miner Metab 17 355-363 (2009); and Landry et al., *The kinetics of thermal instability in nanocrystalline silver and the effect of heat treatment on the antibacterial activity of nanocrystalline silver dressings*, Biomaterials 30 6929-6939 (2009). With the lower exotherm of the silorane biomaterial compositions of the present invention, antimicrobials and growth factors (such cartilage or bone growth factors, e.g., cartilage-derived morphogenic proteins or bone morphogenic proteins) should remain stable. In one aspect, the biomaterial composition contains growth factors selected from the group consisting of TGFβ1, TGFβ2, TGFβ3, BMP-2, BMP-3, BMP-4, BMP-5, BMP-6, BMP-7, BMP-8, BMP-9, CDMP-1, CDMP-2, or CDMP-3.

In another aspect, the biomaterial compositions of the present invention exhibit flexural strength greater than about 20 MPa, and preferably greater than about 50 MPa. For example, the flexural strength may be greater than about 20, 30, 40, 50, 55, 60, or 65 MPa (or have a value of some range therebetween), with higher flexural strengths being preferred. For example, the P1 system (chemical curing system) typically exhibits a flexural strength of about 22 to 33 MPa, and the P2 systems (dual chemical/light curing system) described herein typically exhibit a flexural strength of about 25 to 60 MPa.

In another aspect, biomaterial compositions of the present invention exhibit a flexural modulus greater than 1.5 GPa. For example, the flexural modulus may be greater than about 1.5, 1.6, 1.7, 1.8, 1.9, 2.0, 2.1, 2.2, 2.4, 2.6, 2.8, 3.0, 3.2, 3.4, 3.6, 3.8, or 4.0 GPa (or have a value of some range therebetween). For example, the P1 system (chemical curing system) typically exhibits a flexural modulus of about 1.5 to 1.7 GPa, and the P2 systems (dual chemical/light curing system) typically exhibit a flexural strength of about 2.2 to 3.5 GPa.

In another aspect, the biomaterial compositions of the present invention have a handling time between 5 and 15 minutes (e.g., 5, 6, 7, 8, 9, 10, 11, 12, 13, 14, or 15 minutes (or some range therebetween), and preferably no longer than 20 minutes, when measuring the period of time required for the compositions to harden or "set" according to the Gillmore Needle Test (ASTM C266-89). For example, the P1 system (chemical curing system) and P2 systems (dual chemical/light curing system) described herein typically exhibit a handling time of about 8 to 10 minutes.

Therefore, the present invention is directed to a biomaterial composition which is an alternative to PMAA based bone cements. For example, an ideal bone cement composition will (1) provide a time-efficient means of reducing even small bone fragments to anatomically correct positions; (2) have the same loading response as natural bone; (3) be biocompatible; (4) possess the handling properties to allow for the surgeon/technician to successfully place the material in the fracture site in a controlled manner; and/or (5) not to integrate with the bone, but be easily removed without significantly destroying the tissue. It is anticipated that the biomaterial compositions of the present invention will have one or more of these properties, and preferably all of these properties.

The biomaterial compositions may be used as a bone and dental cement, bone filler, bone anchor, and bone graft in patients. For example, potential applications for the biomaterial composition include, but are not limited to bone cement (the adhesive or material used to join bone fragments together or for placement and anchorage of prosthetic devices); replacement of cartilage found in joints, e.g., knee meniscus, temporomandibular joint, wrist, etc.; vertebroplasty (the augmentation or mechanical support of a compromised vertebrae); bone filler (the material that fills cavities in bone either permanently or temporarily as new bone fills in the defect); bone scaffold; adjunct to metal cages for spinal fixation with screws (the biomaterial may provide additional mechanical support); and support of fractures to non-weight bearing bones (e.g., the orbital bones of the face; and prosthetic spinal disc nucleus). The biomaterial compositions of the present invention may also be used for the delivery of heat sensitive agents—including heat-sensitive antimicrobials and growth factors—due to its low exotherm. For example, the biomaterial compositions—combined with a heat-sensitive antimicrobial or growth factor—may be in the form of a spacer, or as beads or in another vehicular form.

Additional aspects of the invention, together with the advantages and novel features appurtenant thereto, will be set forth in part in the description that follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF PREFERRED EMBODIMENT

Figure 1:
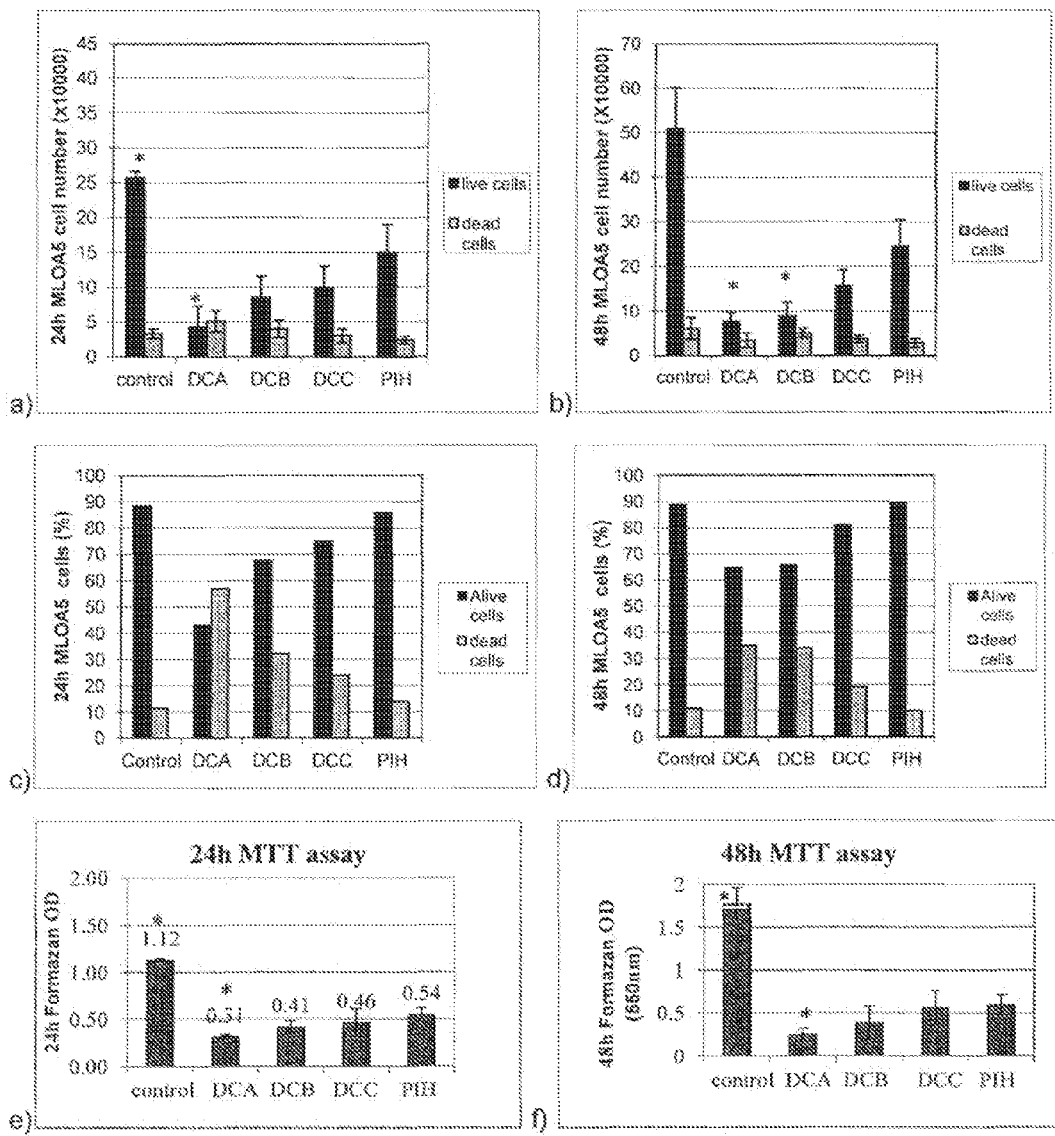
FIG. 1 shows cell growth responses of MLO-A5 cells for chemically cured silorane resins (DCA, DCB, DCC) compared to the light cured silorane resin (PIH) after culturing resins with cells for 24 and 48 hours. Panels a-d are from Trypan blue data and panels e and f are from MTT data. The asterisk (*) defines significantly different values (p<0.05) from the light cure silorane (PIH).

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

The terms "comprises," "comprising," and variations thereof do not have a limiting meaning where these terms appear in the description and claims.

The recitation herein, of numerical ranges by endpoints is intended to include all numbers subsumed within that range (e.g., 1 to 5 includes 1, 1.5, 2, 2.75, 3, 3.80, 4, and 5).

As used herein, "a" or "an" means "at least one" or "one or more" unless otherwise indicated. In addition, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of compounds, measurement of properties, and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

As used herein, the term "patient" encompasses humans and domestic animals including pets and farm animals, exotic animals as found in zoos and similar preserves, and research animals as used in public and private research institutions, e.g., monkeys, chips, cats, dogs, horses, pigs, sheep, cows, monkeys, rats, mice, guinea pigs, and rabbits.

As used herein, the term "chemical cure" refers to a catalytic system capable of catalyzing them polymerization of the organosilicon monomers (preferably silorane monomers) described herein independent of light. While the chemical cure system may optionally include one or more components of a light initiation system (e.g., PIH), the chemical cure system is capable of polymerizing the organosilicon monomers (preferably silorane monomers) in the dark.

As used herein, the term "dual" curing system means and refers to a system that cures at least partially by light-cure (electromagnetic radiation) and at least partially by a chemical cure. As discussed more fully below, the dual chemical/light curing system may contain on or more accelerators, photosensitizers, and/or reaction promoters. Light (typically ultraviolet, visible, or infrared) is needed in order for the complete curing to occur.

Molecular terms, when used in this application, have their common meaning unless otherwise specified. It should be noted that the alphabetical letters used in the formulas of the present invention should be interpreted as the functional groups, moieties, or substituents as defined herein. Unless otherwise defined, the symbols will have their ordinary and customary meaning to those skilled in the art.

The term "alkyl" embraces a branched or unbranched saturated hydrocarbon group of 1 to 12 carbon atoms, such as methyl, ethyl, n-propyl, isopropyl, n-butyl, isobutyl, t-butyl, octyl, decyl, tetradecyl, as well as cyclic alkyl groups and the like.

The term "alkoxy" embraces an alkyl group attached to an oxygen. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, isopropoxy, and tert-butoxy groups.

The term "alkenyl" embraces unsaturated aliphatic groups analogous in length and possible substitution to the alkyls described above, but that contain at least one double bond. Examples include propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, and the like.

The term "alkenoxy" embraces an alkenyl group attached to an oxygen. Examples include allyloxy, 1-propenyloxy, isopropenyloxy, methallyloxy, 2-butenyloxy, 1-butenyloxy, isobutyloxy, pentenyloxy, hexenyloxy, octenyloxy, or decenyloxy.

The term "alkenoxyalkyl" embraces an alkenoxy-substituted alkyl moiety. Examples include allyloxymethyl, allyloxyethyl, allyloxypropyl, and methallyoxymethyl.

The term "aryl" embraces a carbocyclic aromatic system containing one, two, or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, indane, and biphenyl.

The term "arylalkyl" or "aralkyl" embrace aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" embraces aryl groups, as defined above, attached to an oxygen atom, such as phenoxy.

The term "aralkoxy" or "arylalkoxy" embrace aralkyl groups attached through an oxygen atom to other groups. "Lower aralkoxy" groups are those phenyl groups attached to lower alkoxy group as described herein. Examples of such groups include benzyloxy, 1-phenylethoxy, 3-trifluoromethoxybenzyloxy, 4-propylbenzyloxy, and 2-phenylethoxy.

The term silyl refers to the group —$SiH_3$. The silyl group may be optionally substituted with one or more alkyl, aryl, arylalkyl, alkoxy, aryloxy, arylalkoxy groups, or combinations thereof. Thus, for example, the term "alkylsilyl" embraces a silyl group substituted with one or more alkyl groups, such as methylsilyl, dimethylsilyl, trimethylsilyl, ethylsilyl, diethysilyl, triethylsilyl, and the like. The term "arylsilyl" similarly refers to a silyl group substituted with one or more aryl groups, such as phenylsilyl. The term "arylalkylsilyl" refers to a silyl group substituted with one or more arylalkyl groups. The term alkoxysilyl refers to a silyl group substituted with one or more alkoxy groups. The term "aryloxysilyl" embraces silyl groups substituted with one or more aryloxy groups. The term "arylalkoxysilyl" embraces silyl groups substituted with one or more arylalkoxy groups.

The term "siloxy" embraces oxy-containing groups substituted with a silyl group. The siloxy group may be optionally substituted with one or more alkyl, aryl, arylalkyl, alkoxy, aryloxy, arylalkoxy groups, or combinations thereof. Thus, for example, the term "alkylsiloxy" embraces a siloxy group substituted with one or more alkyl groups. The term "arylsiloxy" embraces a siloxy group substituted with one or more aryl groups. The term "arylalkylsiloxy" embraces a siloxy group substituted with one or more arylalkyl groups. The term "alkoxysiloxy" embraces a siloxy group substituted with one or more alkoxy groups. The term "aryloxysiloxy" embraces a siloxy group substituted with one or more aryloxy groups. The term "arylalkoxysiloxy" embraces a siloxy group substituted with one or more arylalkoxy groups.

The term "silylalkyl" embraces silyl-substituted alkyl moieties. The silylalkyl groups may be optionally substituted with one or more alkyl, aryl, arylalkyl, alkoxy, aryloxy, arylalkoxy groups, or combinations thereof. Thus, for example, the term "alkylsilylalkyl" embraces methylsilylpropyl, dimethylsilylpropyl, thmethylsilylpropyl, and the like. The term "arylsilylalkyl" embraces aryl-substituted silylalkyl groups. The term "arylalkylsilylalkyl" embraces arylalkyl substituted silylalkyl groups. The term "alkoxysilylalkyl" embraces alkoxy substituted silylalkyl groups. The term "aryloxysilylalkyl" embraces aryloxy substituted silylalkyl groups. The term "arylalkoxysilylalkyl" embraces arylalkoxy substituted silylalkyl groups.

The term "siloxyalkyl" embraces siloxy-substituted alkyl groups. The siloxyalkyl groups may be optionally substituted with one or more alkyl, aryl, arylalkyl, alkoxy, aryloxy, arylalkoxy groups, or combinations thereof. Thus, the term "alkylsiloxyalkyl" embraces alkyl substituted siloxyalkyl groups. The term "arylsiloxyalkyl" embraces aryl substituted siloxyalkyl groups. The term "arylalkylsiloxyalkyl" embraces arylalkyl substituted siloxyalkyl groups. The term "alkoxysiloxyalkyl" embraces alkoxy substituted siloxyalkyl groups. The term "aryloxysiloxyalkyl" embraces aryloxy substituted siloxyalkyl groups. The term "arylalkoxysiloxyalkyl" embraces arylalkoxy substituted siloxyalkyl groups.

The term "silylalkoxy" embraces silyl-substituted alkoxy groups. The silylalkoxy group may be optionally substituted with one or more alkyl, aryl, arylalkyl, alkoxy, aryloxy, arylalkoxy groups, or combinations thereof. Thus, for example, the term "alkylsilylalkoxy" embraces alkyl substituted silylalkoxy groups. The term "arylsilylalkoxy" embraces aryl substituted silylalkoxy groups. The term "arylalkylsilylalkoxy" embraces arylalkyl substituted silylalkoxy groups. The term "alkoxysilylalkoxy" embraces alkoxy substituted silylalkoxy groups. The term "aryloxysilylalkoxy" embraces aryloxy substituted silylalkoxy groups. The term "arylalkyloxysilylalkoxy" embraces arylalkyloxy substituted silylalkoxy groups.

The term "siloxyalkoxy" embraces siloxy-substituted alkoxy groups. The siloxyalkoxy group may be optionally substituted with one or more alkyl, aryl, arylalkyl, alkoxy, aryloxy, arylalkoxy groups, or combinations thereof. Thus, for example, the term "alkylsiloxyalkoxy" embraces alkyl substituted siloxyalkoxy groups. The term "arylsiloxyalkoxy" embraces aryl substituted siloxyalkoxy groups. The term "arylalkylsiloxyalkoxy" embraces arylalkyl substituted siloxyalkoxy groups. The term "alkoxysiloxyalkoxy" embraces alkoxy substituted siloxyalkoxy groups. The term "aryloxysiloxyalkoxy" embraces aryloxy substituted siloxyalkoxy groups. The term "arylalkoxysiloxyalkoxy" embraces arylalkyloxy substituted siloxyalkoxy groups.

The biomaterial composition of the present invention comprises an organosilicon monomer (such as a silorane) and a chemical curing system or dual chemical/light curing system for polymerizing the monomer. The compositions may also contain TOSUs and/or fillers. The compositions may also include one or more accelerators, such as photoacids. Photosensitizers, and/or reaction promoters may also included in the biomaterial composition having the dual chemical/light curing systems. In addition, one or more pre-polymerized organosilicon monomers may also be included in the biomaterial composition. The pre-polymerized organosilicon monomers essentially function as a filler in the overall biomaterial composition.

In an exemplary aspect, the biomaterial composition comprises about 30 to 60 wt % (e.g., about 30, 35, 40, 45, 50, 55, or 60 wt %—most preferably about 40 to 55 wt %) organosilicon monomer (e.g., silorane co-monomer, such as SilMix); about 0 to 50 wt % (e.g., about 1, 2, 3, 4, 5, 10, 15, 20, 25, 30, 35, 40, 45, or 50 wt %—most preferably about 25 to 50 wt %) pre-polymerized organosilicon monomer (e.g., pre-polymerized silorane filler, such as SilMix); about 0 to 25 wt % (e.g., about 5, 10, 15, 20, or 25 wt %—most preferably about 10 to 20 wt %) other filler (e.g., glass, such as an unmodified glass filler); and about 0.05 to 5 wt % (e.g., about 0.05, 0.06, 0.07, 0.08, 0.09, 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, or 5.0 wt %) of the chemical cure or dual chemical/light curing system. For example, the chemical cure system may comprise about 0.05 to 1.0 wt % (most preferably about 0.05 to 0.2 wt %) p-(octyloxyphenyl)phenyliodonium hexafluoroantimonate and about 0.05 to 1.0 wt % (most preferably about 0.09 to 0.2 wt %) Lamoreaux's catalyst.

As another example, the biomaterial composition comprises about 30 to 60 wt % (e.g., about 30, 35, 40, 45, 50, 55, or 60 wt %—most preferably about 35 to 50 wt %) organosilicon monomer (e.g., silorane co-monomer, such as SilMix) and about 0 to 80 wt % (e.g., about 5, 10, 15, 20, 25, 30, 35, 40, 45, 50, 55, 60, 65, 70, 75, or 80 wt %—most preferably about 45 to 65 wt %) filler (e.g., DY5 filler modified with ECHE, 3TOSU, or 1TOSU); and about 0.05 to 5 wt % (e.g., about 0.05, 0.06, 0.07, 0.08, 0.09, 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, or 5.0 wt %) of the chemical cure or dual chemical/light curing system. For example, the dual chemical/light curing system may comprise about 0.05 to 1.0 wt % (preferably about 0.3 to 0.8 wt %) Lamoreaux's catalyst and a photoinitiation system comprising about 1 to 5 wt % of an accelerator (e.g., about 3 wt % PIH), about 0.05 to 2 wt % photosensitizer (e.g., about 1 wt % camphorquinone), and 0.05 to 0.5 wt % electron donor (e.g., about 0.15 wt % EDMAB).

As another example, the biomaterial composition comprises about 20 to 98 wt % (e.g., about 30, 35, 40, 45, 50, 55, 60, 65, 60, 65, 70, 75, 80, 85, 90, 91, 92, 93, 94, 95, 96, 97, 98 wt %—most preferably about 90 to 98 wt % for the "neat" biomaterial composition) organosilicon monomer (e.g., silorane co-monomer, such as SilMix); about 0 to 80 wt % (e.g., about 5, 10, 15, 20, 25, 30, 35, 40, 45, 50, 55, 60, 65, 70, 75, or 80 wt %—most preferably about 45 to 65 wt %) filler (e.g., DY5 filler modified with ECHE, 3TOSU, or 1TOSU); and about 0.05 to 5 wt % (e.g., about 0.05, 0.06, 0.07, 0.08, 0.09, 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, or 5.0 wt %) of the chemical cure or dual chemical/light curing system. For example, the dual chemical/light curing system may comprise a mixture and acid (preferably a Bronsted acid), photoacid, and a photosensitizer. The ratio of the Bronsted acid to the photoacid is preferably between about 3:1 to 1:3 by weight (e.g., about 3:1, 2:1, 1:1, 1:2, and 1:3). The ratio of the Bronstead acid to the photosensitizer is preferably about 10:1 to 1:1 by weight (e.g., about 10:1, 8:1, 5:1, 3:1, and 1:1). In an exemplary aspect, the biomaterial composition may comprise a dual chemical/light cure system comprised of acetic acid, PIH, and camphorquinone at a ratio of about 3:3:1 percent by weight, e.g., about 3 wt % acetic acid, 3 wt % PIH, and 1 wt % camphorquinone (for a neat biomaterial composition containing no filler) and 1.5 wt % acetic acid, 1.5% PIH, and 0.5% camphorquinone (for a 50% filled biomaterial composition).

Each of the components of the composition of the present invention will now be described in further detail.

Organosilicon Monomers

Various organosilicon monomers useful in the biomaterial compositions of the present invention are set forth in Chappelow, U.S. Published Patent Application No. 2007/0072954; Weinmann et al., U.S. Pat. No. 6,908,953; Weinmann et al., U.S. Pat. No. 6,245,828 entitled "Polymerizable Compositions Based on Epoxides" and Bissinger et al., U.S. Pat. No. 6,624,236 entitled "Cyclosiloxane-Based Cross-Linkable Monomers, Production Thereof in Polymerizable Materials;" Weinmann et al., Siloranes in dental composites, Dent. Mater. 21(1) 68-74 (2005); Eick et al., Properties of silorane-based dental resins and composites containing a stress-reducing monomer, Dent. Mater. 23(8) 1011-1017 (2007); all of which are incorporated by reference. Most preferred organosilicon monomers are "siloranes," which generally refer to silicon-containing monomers having an oxirane (epoxide) and preferably a siloxane (e.g., Si—O bond or Si—O—Si—O).

A variety of organosilicon compounds with oxirane functionality were first synthesized and polymerized by Sato et al., JP Patent No. 51033541 (Sep. 20, 1976). Similar compounds were studied by Crivello and others. See Crivello et al., European Patent No. 574264 (1993); and Crivello et al., European Patent No. 412430 (1991), which are incorporated by reference. Most preferred are multifunctional cycloaliphatic siloxane-based oxiranes. Exemplary organosilicon monomers useful for forming the dental matrix resins of the present invention include di-3,4-epoxy cyclohexylmethyl-dimethyl-silane (DiMe-Sil; $R^N$ 349660-80-6; MF, $C_{16}H_{28}O_2Si$; 95% purity), 1,4-bis(2,3-epoxypropyloxypropyl-dimethylsilyl)benzene (Phen-Glyc: RN 18715-54-3; MF, $C_{22}H_{38}O_4S_{i2}$; 97% purity), and 1,3,5,7-tetrakis(ethyl cyclohexane epoxy)-1,3,5,7-tetramethyl cyclotetrasiloxane (CYGEP: RN 121225-98-7; MF, $C_{36}H_{64}O_8S_{i4}$; 98% purity), all available from 3M-ESPE (St. Paul, Minn.). Exemplary siloranes are set forth in Weinmann et al., Volume shrinkage of a new filling material based on siloranes, J. Dent. Res. 80(SI) 780 Abstr. No. 2027 (2001); Weinmann et al., Comparative testing of volumetric shrinkage and sealing of silorane and methacrylate filling materials, J. Dent. Res. 81(SI-A) 417 Abstr. No. 3382 (2002); Dede et al., Comparison of two ways to determine polymerization shrinkage of composites, J. Dent. Res. 83(SI-A) Abstr. No. 0057 (2004); Guggenberger et al., Exploring beyond methacrylates, Am J Dent. 13 82D-84D (November 2000); Schwekl, The induction of gene mutations and micronuclei by oxiranes and siloranes in mammalian cells in vitro, J. Dent. Res. 83(1) 17-21 (January 2004); Eick et al., Stability of silorane dental monomers in aqueous systems, J. Dent. 34(6) 405-410 (2006), Watts, Shrinkage-Stress Kinetics of Silorane versus Dimethacrylate Resin-Composites, 12 Baltimore Convention Center 322-323 (Abstract) (March 2005); and Klettke et al., U.S. Pat. No. 6,779,656, which are all incorporated by reference.

Combinations of organosilicon monomers may also be utilized in the biomaterial compositions of the present invention. For example, SilMix is comprised of a 1:1 w/w (2:1 mol/mol) ratio of methylbis[2-(7-oxabicyclo[4.1.0]hept-3-yl)ethyl]phenylsilane I ("PHEPSI") and 2,4,6,8-tetramethyl-2,4,6,8-tetrakis-[2-(7-oxabicyclo[4.1.0]hept-3-yl)ethyl]-1,3,5,7-tetraoxa-2,4,6,8-tetrasilacyclooxtane II ("CYGEP") produced by 3M-ESPE (St. Paul, Minn.). The structures SilMix compounds are shown below:

I

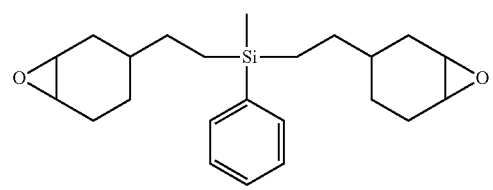

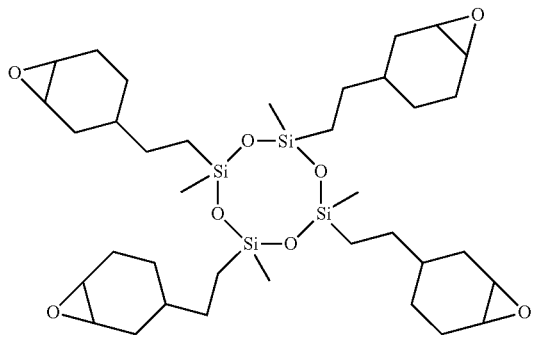

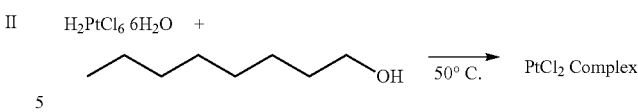

The organosilicon monomers used in the biomaterial compositions of the present invention are preferably prepared at purities greater than 90%, and most preferably greater than 95% as determined by $^1$H NMR spectroscopy.

The organosilicon monomers preferably comprises about 20 to 98 wt % (e.g., about 20, 30, 40, 50, 60, 70, or 80%), and in some aspects, more preferably about 40 to 60 wt % of the composition. Furthermore, as discussed below, the monomers may be pre-polymerized prior to addition to the composition so that the biomaterial composition comprises both unpolymerized monomers and pre-polymerized polymer prior to polymerization. Typically, the ratio of unpolymerized monomers (e.g., SilMix co-monomer) to polymer (e.g., pre-polymerized SilMix) is about 1:5 to 5:1 (e.g., about 1:5, 1:4, 1:3, 1:2, 1:1, 2:1, 3:1, 4:1, or 5:1, or some range therebetween). For biomaterial compositions containing pre-polymerized organosilicon monomers, the polymer is preferably crushed or ground to a particle size (typically irregular in shape) of about 0.5 to 15 µm (e.g., 0.5, 1, 3, 5, 7, 9, 11, 13, or 15 µm, or some range therebetween) with a number average size of about 2 µm. The pre-polymerized organosilicon monomer essentially functions as a filler in the overall composition.

Cure/Initiation Systems

The biomaterial compositions of the present invention also include a chemical cure/initiation system or a dual chemical/light curing system.

1. Chemical Cure/Initiation System

In one aspect, the chemical curing system comprises a hydrosilation catalyst which may be used to effect the addition of the ethylenically unsaturated epoxide or epoxide/organic mixture. Preferred catalysts are those taught by Lamoreaux in U.S. Pat. Nos. 3,917,432; 3,197,433; and 3,220,972, which are all hereby incorporated by reference. The platinum catalyst disclosed in the patents to Lamoreaux is a complex formed from chloroplatinic acid with up to about 2 moles per gram of platinum of a member selected from the class consisting of alcohols, ethers, aldehydes, and mixtures of the above. This catalyst will sometimes be referred to herein as the "Lamoreaux catalyst."

In a preferred aspect, the chemical curing system comprises a Lamoreaux's catalyst which involves either $PtCl_2$ with aldehyde and ether linkages derived from octanol. This catalyst was synthesized from chloroplatinic acid $H_2PtCl_6$ using an adapted procedure by Lamoreaux, U.S. Pat. No. 3,220,972, which is incorporated by reference.

In one aspect, Lamoreaux's catalyst may be prepared by heating the reaction mixture to 70° C. at 25 mm Hg for 40 hours as discussed in the patent references. In another aspect, Lamoreaux's catalyst may be prepared by heating the reaction mixture (chloroplatinic acid hexahydrate and octanol (98%) combined in a 1:7 mole ratio) to 50 to 55° C. under vacuum at 0.01 mm Hg for about 40 to 42 hours. After that time, the solution was filtered and washed with hexanes. The filtrate was placed under vacuum (0.01 mm Hg) at room temperature for about 8 to 12 hours. The resulting liquid was stored under inert atmosphere in the refrigerator.

Further, other organometallic catalysts, such as those containing ruthenium, rhodium, iridium, palladium, platinum, iron, osmium, cobalt, molybdenum, tungsten, nickel, copper, gold, silver, zirconium, and titanium (most preferably Pt and/or Rh) are also possibilities for chemical curing. For example, for platinum-based catalysts, Wilkinson's catalyst, Speier's catalyst, and Karstedt's catalyst may also be employed, while Grubb's catalyst may be a suitable ruthenium-based catalyst.

The chemical curing system may optionally contain an accelerator. A preferable accelerator is a photoacid, such as those described in Akizumi et al., U.S. Published Patent Application No. 2011/0172323, which is incorporated herein by reference. Most preferred accelerators are aryl-based iodonium salts, in particular a phenyl iodonium salt. Examples of such accelerators include, but are not limited to, (4-n-octyloxyphenyl)phenyliodonium hexafluoroantimonate ("PIH"), which may be obtained from GE Silicones under number 479-2092C; [4-(2-hydroxytetradecyloxyphenyl)]phenyliodonium hexafluoroantimonate (CD 1012), which may be obtained from Sartomer under the trade name SarCat CD-1012 or from Gelest under the trade name OMAN072; [4-1-methylethyl)phenyl](4-methylphenyl)iodonium tetrakis(pentafluorophenyl)borate(1−) (RH02074), which may be obtained from Rhodia, Inc., under the trade name Rhodorsil Photoinitiator 2074; and combinations thereof. See also, similar compounds discussed in Yamtao et al., WO 2002/046507, which is incorporated by reference. Although such accelerators have been traditionally used in light initiated polymerization systems, they also may be used in the chemical-initiated polymerization composition of the present invention. The mechanism by which the photoacid (e.g., PIH) reacts with the organometallic catalyst (e.g., Lamoreaux's catalyst) to permit polymerization in the dark when using this exemplary chemical curing system of the present invention is not known.

It will be appreciated that chemical curing system does not require a photosensitizer or reaction promoter (although such compounds could optionally be included in the composition).

The chemical curing system preferably comprises about 0.05 to 2 wt % (e.g., 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 wt %) of the biomaterial composition. For example, the chemical cure system may comprise about 0.1 to 1.0 wt % of the photoacid (e.g., about 0.05 to 0.4 wt %, preferably about 0.05 to 0.2 wt %, of p-(octyloxyphenyl) phenyliodonium hexafluoroantimonate) and about 0.05 to 1.0 wt % organometallic catalyst (e.g., about 0.1 to 0.4 wt %, preferably about 0.09 to 0.2 wt % Lamoreaux's catalyst).

2. Dual Chemical/Light Cure/Initiation System

In another aspect, the biomaterial compositions of the present invention comprise a dual chemical/light cure system. One exemplary dual chemical/light cure system comprises a mixture of a chemical curing agent (such as an acid or one of the organometallic catalysts referenced herein), along with an accelerator (see examples above), photosensitizer, and/or reaction promoter.

Chemical Curing Agent (e.g. Acetic Acid Containing Systems)

The dual chemical/light cure system may include an acid. In the present invention, various Lewis aids, Bronsted acids, and super acids were investigated. The acids investigated included hydrochloric acid, acetic acid ("AA"), phosphoric acid, sulfuric acid, hydrobromic acid, hydroiodic acid, trichloroacetic acid, trifluoroacetic acid, p-toluenesulfonic acid, boron trifluoride, aluminium chloride, tin (IV) chloride, titanium chloride, pentafluoroproprionic acid, triflic acid, hexafluorophosphoric acid ("HFPA"), ethyl triflate, potassium t-butoxide, and mixtures thereof (e.g., AA/HFPA, phosphoric acid/TiCl$_4$, phosphoric acid/triflic acid, phosphoric acid/p-toluene sulfonic acid, and phosphoric acid/trifluoroacetic acid).

The preferred acid investigated is acetic acid. Thus, in one aspect, the preferred acid is a weak/mild monoprotic acid which is nontoxic and biocompatible. The acid preferably has a pKa between about 3 and 6 (e.g., 3, 4, 5, or 6), exhibits low volatility, and is soluble in the organic monomers being polymerized.

Photosensitizer

The dual curing system also preferably includes one or more photosensitizers. Exemplary photosensitizers are disclosed in Chappelow et al., U.S. Pat. No. 6,653,486, which is incorporated by reference. Suitable sensitizers include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones, and p-substituted aminostyryl ketone compounds are preferred sensitizers. For example, such photosensitizers include, but are not limited to as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m-, and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones include 2,3-butanedione, 2,3-pentanedione, 2,3-hexanedione, 3,4-hexanedione, 2,3-heptanedione, 3,4-heptanedione, 2,3-octanedione, 4,5-octanedione, benzyl, 2,2'-3,3'- and 4,4'-dihydroxylbenzyl, furyl, di-3,3'-indolylethanedione, 2,3-bomanedione (camphorquinone), biacetyl, 1,2-cyclohexanedione, 1,2-naphthaquinone, acenaphthaquinone, and the like.

A preferred photosensitizer is an alpha-dicarbonyl compound. Examples of specific photosensitizers that may be used in the composition of the present invention include, but are not limited to, (+/−) camphorquinone, which may be obtained from Aldrich under the number 12, 489-2 with a 97% purity; 2-chlorothioxanthen-9-one ("CTXO"), which may be obtained from Aldrich C7-240-4; and combinations thereof.

Reaction Promoter (Electron Donor)

Another preferred component of the dual chemical/light curing system is one or more electron donor compounds, which functions as a reaction promoter. A class of donor compounds that may be useful in the inventive systems may be selected from some of the electron donors described in Chappelow et al., U.S. Pat. No. 6,653,486 and Palazzotto et al., U.S. Pat. No. 5,545,676, which are both incorporated by reference. Preferred electron donor compounds include substituted amines, e.g., ethyl dimethylaminobenzoate. The preferred electron donor that may be used in the composition of the present invention include, but are not limited to, ethyl p-dimethylaminobenzoate ("EDMAB"), which may be obtained from Acros under number 11840-1000 at 99+% purity; 4,4'-bis(diethylamino)benzophenone ("BDEAB"), which also may be obtained from Acros under number 17081-0250s at 99+% purity; and combinations thereof.

The dual chemical/light curing system preferably comprises about 0.05 to 5 wt % (e.g., 0.05, 0.06, 0.07, 0.08, 0.9, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, or 5.0 wt %) of the biomedical composition.

Exemplary Dual Chemical/Light Curing Systems

In exemplary embodiments, the dual chemical/light curing system may comprise 0.05 to 0.2 wt % (preferably about 0.3 to 0.8 wt %) Lamoreaux's catalyst and a photoinitiation system comprising about 1 to 5 wt % of an accelerator (e.g., about 1, 1.5, 2, 2.5, 3, 3.5, 4, 4.5 or 5 wt %, preferably about 3 wt % PIH), about 0.05 to 2 wt % photosensitizer (e.g., about 0.05, 1, 1.5, 2 wt %, preferably about 1 wt % camphorquinone), and 0.05 to 0.5 wt % electron donor (e.g., 0.05, 0.1, 0.15, 0.2, 0.25, 0.3, 0.35, 0.4, 0.45, 0.5 wt %, preferably about 0.15 wt % EDMAB).

In another exemplary aspect, the dual chemical cure system comprises an acid (e.g., acetic acid), a photosensitizer (e.g., camphorquione), and a photoacid (e.g., PIH). The ratio of the Bronsted acid to the photoacid is preferably between about 3:1 to 1:3 by weight (e.g., about 3:1, 2:1, 1:1, 1:2, and 1:3). The ratio of the Bronstead acid to the photosensitizer is preferably about 10:1 to 1:1 by weight (e.g., about 10:1, 8:1, 5:1, 3:1, and 1:1). For example, the composition may comprise a dual chemical/light cure system comprised of acetic acid, PIH and camphorquinone at a ratio of about 3:3:1 percent by weight. For example, the composition may comprise about 1.5 wt % acetic acid, 1.5% PIH, and 0.5% camphorquinone (for a 50% filled composition). The percentage by weight is preferably 3:3:1 of AA:PIH:CQ.

Fillers

The biomaterial compositions may further comprise one or more fillers. These fillers can possess a variety of morphologies such as, but not limited to, needles, rods, particulate, flakes, plates, cylinders, long fibers, whiskers, or spherical particles. In some embodiments that may be preferred, the filler is comprised of particles with an average particle size which is in the sub-micron or nanoparticle range, e.g., less than about 1.0 μm. Exemplary particle sizes are about 10, 20, 30, 40, 50, 60, 70, 80, 90, 100, 150, 200, 250, 300, 350, 400, 450, 500, 600, 700, 900, or 1000 nm or some range therebetween.

Given the appropriate interactions and dispersion qualities, particle size may be a critical factor in that nanoparticles can produce dramatic changes in the mechanical properties of the composition as compared to micrometer sized fillers at comparable volume loading to analogous nanoparticle composites. For example, improvements in tensile strength and modulus of five- and seven-fold may be obtained for composites containing only 1.5% nanoclay particles. Similar low loadings with resulting increased properties have been reported elsewhere. Surprisingly, higher concentrations of nanoparticles made little further improvement. Improved strength and wear properties at low filler volume loading are anticipated if the particles are not subject to being ablated from the matrix, i.e., are prevented from discreet particle ablation by covalent bonding of the particles into the polymer matrix.

The filler may be comprised of an inorganic or organic material, which may be bioactive. In certain embodiments, the filler is comprised of an inorganic material.

Suitable fillers may be particulate or fibrous fillers with sizes in the nanoparticle to microparticle range. Fillers should be capable of being covalently bonded to the resin matrix itself or to a coupling agent that provides bonding to the filler and then the surrounding resin matrix. Examples of suitable filling materials include but are not limited to amorphous silica; spherical silica; colloidal silica; clays; barium glasses; quartz; ceramic fillers; silicate glass; hydroxyapatite; calcium carbonate; fluoroaluminosilicate; barium sulfate; quartz; barium silicate; strontium silicate; barium borosilicate; barium boroaluminosilicate; strontium borosilicate; strontium boroaluminosilicate; bio active glass; dental glass ionomer filler; silicate or phosphate based glass fibers; lithium silicate; ammoniated calcium phosphate; deammoniated calcium phosphate; calcium tungstate; alumina; zirconia; tin oxide; zinc oxide; calcium oxide; magnesium oxide, postassium oxide, barium oxide yttrium oxide, bismuth compounds such as bismuth oxychloride and bismuth oxide; polymer powders such as polymethyl methacrylate, polystyrene, and polyvinyl chloride; titanium dioxide; bound and nano structured silica fillers as set forth in U.S. Pat. No. 6,417,246, which is hereby incorporated by reference; densified and embrittled glass fibers or particles as set forth in U.S. Pat. Nos. 6,013,694 and 6,403,676 which are hereby incorporated by reference; fibrous material and one or more forms of surface-modifying particles bonded thereto as set forth in U.S. Pat. No. 6,270,562 which is hereby incorporated by reference; polyhedral oligomeric silsesquioxane fillers as set forth in U.S. Pat. No. 6,653,365 which is hereby incorporated by reference; nanostructures such as POSS™ (polyhedral oligomeric silsesquioxane) supplied by Hybrid Plastics; and combinations of all the fillers mentioned. Preferred fillers include titanium oxide and/or calcium phosphate since these materials help promote mineralization and bone adhesion. Composition of the macro and micro fillers will not be identical or perhaps even similar. Nanoparticles will be typically high purity, high strength whiskers/rod/fibers/platelets, while the macrofiller will typically be a silica-based ally glass with additive elements for strength and hardness.

In another aspect, examples of suitable fillers include, but are not limited to, barium glass, barium-boroaluminosilicate glass, sodium borosilicate, silica, 45S5 glass, bioactive glass, ceramics, glass-ceramics, bioactive synthetic combeite glass-ceramic, e-glass, s-glass, iron phosphate, or combinations thereof. The most preferred fillers are yttria alumino silicate (e.g., DY5; see table below) and barium boroaluminosilicate (e.g., M12, see table below), and alumina or zirconia nanorods.

Preferred glass fillers can be made by either melting batches (M-series and alkali-containing DY-series) or by sintering batches and spheroidization of the sinter (alkali-free DY-series). The sinter/spheroidization process was used for batches that melted above 1550° C. The nominal chemical composition and $n_d$ of the M-series glasses are given in Table 1 below. The nominal chemical composition and $n_d$ of the DY-series glasses are listed in Table 2 below. The $n_d$ of the glasses varied from 1.48 to 1.56 depending on composition, a range of values which is needed for reinforcing blue-light (440 nm)-curable composites.

TABLE 1

Nominal Weight Percent Composition and Refractive Index of M-Series

| Filler Code | $Li_2O$ | $Na_2O$ | $K_2O$ | MgO | BaO | CaO | $Y_2O_3$ | $ZrO_2$ | $Yb_2O_3$ | ZnO | $TiO_2$ | $B_2O_3$ | $Al_2O_3$ | $SiO_2$ | $AlF_3$ | $n_d$ |
|---|---|---|---|---|---|---|---|---|---|---|---|---|---|---|---|---|
| M1 | 3 | 0 | 0 | 2 | 9 | 0 | 3 | 0 | 0 | 0 | 0 | 58 | 14 | 8 | 3 | 1.53 |
| M2 | 3 | 0 | 0 | 2 | 9 | 0 | 3 | 0 | 0 | 0 | 0 | 29 | 14 | 37 | 3 | 1.52 |
| M3 | 3 | 0 | 0 | 2 | 9 | 0 | 0 | 0 | 3 | 0 | 0 | 29 | 14 | 37 | 3 | 1.52 |
| M4 | 3 | 0 | 0 | 2 | 9 | 0 | 3 | 0 | 0 | 0 | 0 | 58 | 0 | 22 | 3 | 1.53 |
| M5 | 0 | 1 | 0 | 8 | 0 | 0 | 0 | 9 | 0 | 0 | 0 | 0 | 21 | 61 | 0 | 1.52 |
| M6 | 0 | 1 | 0 | 2 | 0 | 22 | 0 | 5 | 0 | 0 | 0 | 7 | 11 | 52 | 0 | 1.56 |
| M7 | 0 | 10 | 0 | 1 | 0 | 6 | 0 | 22 | 0 | 0 | 0 | 3 | 4 | 54 | 0 | 1.56 |
| M8 | 0 | 6 | 8 | 0 | 2 | 6 | 0 | 5 | 0 | 5 | 0 | 0 | 2 | 66 | 0 | 1.52 |
| M9 | 0 | 5 | 6 | 0 | 0 | 0 | 0 | 5 | 0 | 7 | 4 | 8 | 4 | 61 | 0 | 1.52 |
| M10 | 3 | 0 | 0 | 2 | 9 | 0 | 3 | 0 | 0 | 0 | 0 | 58 | 14 | 8 | 3 | 1.52 |

TABLE 2

Nominal Weight Percent Composition and Refractive Index of DY-Series Glasses

| Filler Code | $Y_2O_3$ | $Yb_2O_3$ | $Al_2O_3$ | $SiO_2$ | $Na_2O$ | $n_d$ |
|---|---|---|---|---|---|---|
| DYb1 | 0 | 23 | 21 | 56 | 0 | 1.55 |
| DY2 | 1 | 0 | 9 | 90 | 0 | 1.48 |
| DY3 | 3 | 0 | 9 | 88 | 0 | 1.48 |
| DY4 | 15 | 0 | 21 | 64 | 0 | 1.56 |
| DY5* | 15 | 0 | 5 | 80 | 0 | 1.52 |
| DY6 | 15 | 0 | 15 | 70 | 0 | 1.53 |
| DY7 | 14 | 0 | 14 | 67 | 5 | 1.52 |
| DY8 | 14 | 0 | 14 | 62 | 10 | 1.51 |
| DY9 | 13 | 0 | 13 | 59 | 15 | 1.53 |
| DY10 | 0 | 23 | 21 | 56 | 0 | 1.52 |

*Vickers microhardness 6.2 GPa (739 ± 22 kg/mm$^2$)

Nanoparticles assist cement formulation, reinforcing and strengthening the interstitial domains within the composition, obtaining radiopacity when not obtained via the macrofiller, and hardening the surface against wear by increasing the filler volume concentration. While spherical or irregular nanoparticles are used in current formulations, whisker/nanorods and/or clay platelets may also be used for interstitial strengthening of the macroparticle filled composite where obtained at low filler volume loading. An increased aspect ratio is important to mechanical strength, minimization of crack initiation, and can support mineralization by osteoblast cells though spherical or irregular nanoparticles that can also be utilized to reinforce the interstitial composite so long as a suitable surface modification or coupling agent is utilized to strengthen bone across the polymer-particle interface. Clay/nanowhisker/nonrod dimensions are preferred that have aspect ratios greater than 10:1 up to about 100:1. Clays include montmorillonites and nanowhisker/nanorod includes boehmite, alumina, zirconia, yttria-stabilized zirconia, titania, calcium phosphate, or hydroxyl apatite.

Surface modifications can be used to control interparticle association, dispersion viscosity, and reactivity with the surrounding matrix. In one aspect, nanospheres or nanofillers, typically up to 500 nm in length and 30 nm in diameter may be used. Normal, glass filled systems can also be used for dispersion quality, flexural strength, hardness, internal polymerization stress, efficiency of cure, and cell toxicity of the resulting composite. Compositions of the nanofibers include alumina nanospheres and nanorods, which have produced improved tensile and flexural strength. While alumina has provided remarkable property improvements, zirconium-yttrium oxide fiber synthesis, whose fibers have better pH stability compared to alumina, may also be used. Nanorods will be synthesized via gel formation followed by chemically templating in conventional oven or by autoclave, as appropriate for the desired geometry.

Montmorillonite clays are the most common member of the smectite clay family having plate-like primary particles that possess an anionic surface with ionically bound cations to maintain surface charge neutrality. Natural montmorillonite clay has sodium counterions on the surface; however, these sodium atoms can be ion-exchanged with other inorganic or organic ions to change the surface chemistry of the clay particles. In addition, natural montmorillonite clay particles are stacked upon one another due to the charge-charge interaction between the clay platelets. Once the counterion is exchanged for an organic ion or group, the replacement facilitates the separation of the clay lattice, especially when penetrated by solvents, monomer or polymer chains, called intercalation. The particles may then be further dispersed into discreet nanoplatelets resulting in what is called an exfoliated clay material. Upon synthesis of exfoliated structures, large mechanical property improvements of a composite compared to neat polymer properties are obtained at rather low clay filler concentration levels.

Such fillers include, but are not limited to, a hydroxyapatite in the form of hollow microspheres or biocompatible, biodegradable glass. The microspheres of hydroxyapatite could be used to contain and act as carriers for antibiotics. Other components of the composites that could be delivered within the hydroxyapatite microspheres include growth factors such as bone morphogenetic proteins ("BMPs"), cartilage-derived morphogenic proteins ("CDMPs"), collagen, or small molecules that are being developed to promote bone growth through blood vessel formation. In one aspect, the growth factor is selected from the group consisting of TGFβ1, TGFβ2, TGFβ3, BMP-2, BMP-3, BMP-4, BMP-5, BMP-6, BMP-7, BMP-8, BMP-9, CDMP-1, CDMP-2, or CDMP-3.

For silorane composites, good interfacial properties between polymer resin and fillers improve composite properties and performance. There are variables of group density and structure, which affect surface wetting, reactivity, interfacial structure, and composite strength. The inclusion of a surface coupling agent or ligand increases the critical concentration of particle fillers that can be added by enhancing surface wetting and dispersion viscosity. Interfacial properties are even more critical since the intended application requires immersion within a plasticizing, high-moisture environment. Interfaces between filler and resin matrix are prime locations for weakening through ingress of moisture. However, interfaces can be strengthened through surface modification of fillers resulting in greater mechanical properties to enable not only interaction, but also reaction with the surrounding polymer matrix, including chain extension, between filler and polymer matrix. Several types of surface modifications may be used to improve strength through development of covalent interface architectures during cure. Surface modifications are produced through exposure to dilute solutions to prevent multi-layer, weak, adsorbed structures and provide better ligand access to filler surfaces. After washing particles thoroughly of excess reagent, groups are quantified by thermogravimetric analysis (TGA) for comparison to bare particles. Fourier transform infrared spectroscopy (FTIR), X-ray photoelectron spectroscopy (XPS), and surface density calculated from weight loss using known particle surface area and correcting for bulk and adsorbed water loss is used to analyze the filler surface coating. Surface tension and wetting of filler powders is readily measured using tensiometry through the Washburn equation.

The filler typically is about 0, 5, 10, 15, 20, 25, 30, 40, 45, 50, 55, 60, or 70 wt % (or some range therebetween) of the biomaterial composition.

TOSUs and TOSU-Like Compounds

TOSUs may optionally be added to the biomaterial compositions of the present invention. The TOSUs may be classified as 1,5,7,1'-tetraoxaspiro[5.5]undecanes or 2,4,8,10-tetraoxaspiro[5.5]undecanes. The TOSUs may or may not have a silicon-containing moiety. The TOSUs are preferably a potential expanding monomer type. By using the TOSUs, the composition has the potential of reducing the amount of polymerization stress of the total formulation.

Various TOSUs are set forth in Chappelow, U.S. Published Patent Application No. 2007/0072954; Chappelow et al., U.S. Pat. No. 6,825,364; Chappelow et al., U.S. Pat. No. 6,653, 486; Chappelow et al., U.S. Pat. No. 6,658,865; Byerley et al., U.S. Pat. No. 5,556,896; Guest, U.S. Pat. No. 3,023,2221; Sadhir & Luck, *Expanding Monomers: Synthesis, Characterization, and Applications*, CRC Press, Boca Raton, Fla. (1992); Rokicki, *Aliphatic cyclic carbonates and spiroorthocarbonates as monomers*, Prog. Polym. Sci. 25 259-342 (2000); Imai et al., JP 28196665B2; and Porret et al., JP 03099086; which are all incorporated by reference. An important synthetic precursor is 3,9-diethyl-3,9-bis(allyloxymethyl)-1,5,7,11-tetraoxaspirol[5.5]undecane (DE-BAOM-1,5,7,11-TOSU), and is a six-member ring spiroorthocarbonate that is a liquid at room temperature. The vinyl groups on this molecule permit the addition of a wide variety of reactive and unreactive functionalities by electrophilic and radical means. These functionalities can be both symmetric and asymmetric.

In one aspect of the present invention, TOSUs according to Formulas A1 or A2 may be utilized in the biomaterial compositions:

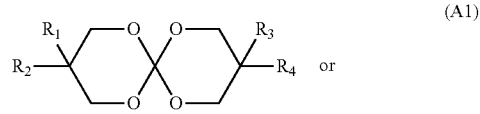
(A1)

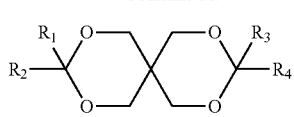
(A2)

wherein $R_1$ and $R_3$ are independently is alkyl, aryl, aralkyl, or hydrogen; and wherein $R_2$ and $R_4$ are independently alkenoxy, alkenoxyalkyl, or silicon-containing moiety selected from alkylsilyl, arylsilyl, arylalkylsilyl, alloxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy, arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy.

In another aspect, the TOSUs are characterized by Formulas A1 or A2 wherein $R_2$ and $R_4$ are independently alkylsilylalkyl or alkylsiloxyalkyl. In one preferred aspect, $R_2$ and $R_4$ are independently trimethylsilylpropyl, trimethylsilylethyl, triethylsilyipropyl, or triethylsilylethyl.

In still another aspect, the TOSU compounds according to Formula A1 or A2 are characterized such that $R_1$ and $R_3$ are independently is alkyl, aryl, aralkyl, or hydrogen; and wherein $R_2$ and $R_4$ are independently alkenoxyalkyl or alkylsilylalkyl. In still another aspect, $R_2$ and $R_4$ are independently alkenyloxyalkyl selected from —$(CH_2)_n$—O—$(CH_2)_m$—CH=$CH_2$, and wherein m and n are independently 0, 1, 2, 3, 4; or alkylsilylalkyl selected from trimethylsilylpropyl and trimethylsilylethyl.

In another aspect, the TOSU compounds according to the Formula A2 are characterized such that $R_1$ and $R_3$ are independently alkyl, aryl, aralkyl, or hydrogen; and wherein $R_2$ and $R_4$ are independently alkenyl, alkenoxy, alkenoxyalkyl, or silicon-containing moiety selected from alkylsilyl, arylsilyl, arylalkylsilyl, alloxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkoxysiloxyalkoxy, arylsiloxyalkoxy, arylalkylsiloxyalkoxy, alkoxysiloxyalkoxy, aryloxysiloxyalkoxy, and arylalkoxysiloxyalkoxy.

In another aspect, the TOSU compounds according to the Formula A1 or A2 are characterized such that $R_1$ and $R_3$ are independently alkyl, aryl, aralkyl, or hydrogen; and wherein $R_2$ and $R_4$ are independently alkenyl, alkenoxyalkyl, and alkylsilylalkyl. In still a further aspect, $R_2$ and $R_4$ are independently alkenyl selected the group consisting of —$(CH_2)_n$—CH=$CH_2$, and wherein n is independently 0, 1, 2, 3, 4; or alkenyloxyalkyl selected from —$(CH_2)_n$—O—$(CH_2)_n$—CH=$CH_2$, and wherein m and n are independently 0, 1, 2, 3, 4; or alkylsilylalkyl selected from trimethylsilylpropyl and trimethylsilylethyl.

In another aspect, $R_1$, $R_2$, $R_3$, and $R_4$ are independently selected from the group consisting of alkyl, olefin-terminated alkyl, olefin-terminated alkyl ether, trimethylsilyl alkyl ether, and cyclohexyl.

For example, in one aspect, the TOSUs are selected from the group consisting of the following compounds:

3,9-Diethyl-3,9-bis(allyloxymethyl)-1,5,7,11-tetraoxaspirol[5.5]undecane (DEBAOM-1,5,7,11-TOSU) (Example 1 of Chappelow, U.S. Published Patent Application No. 2007/0072954)

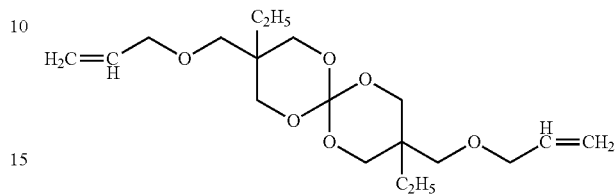

9-Bis(3-trimethylsilylpropyl)-1,5,7,11-tetraoxaspiro[5.5]undecane (BTMSP-1,5,7,11-TOSU) (Example 2 of Chappelow, U.S. Published Patent Application No. 2007/0072954)

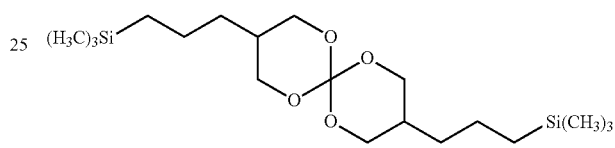

3,9-Bis(allyloxymethyl)-2,4,8,10-tetraoxaspiro[5.5]undecane (BAOM-2,4,8,10-TOSU) (Example 3 of Chappelow, U.S. Published Patent Application No. 2007/0072954)

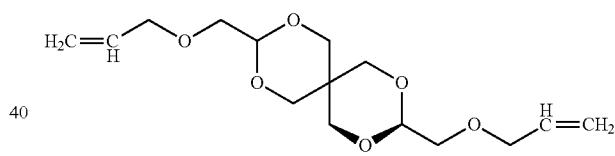

3,9-Bis(2-trimethylsilylethyl)-2,4,8,10-tetraoxaspiro[5.5]undecane (BTMSE-2,4,8,10-TOSU) (Example 4 of Chappelow, U.S. Published Patent Application No. 2007/0072954)

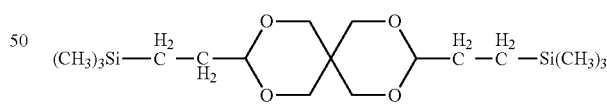

3,3-Diethyl-11,12-epoxy-1,5,7,16-tetraoxadispiro[5.2.5.2]hexadecane (DECHE-1,5,7,11-TOSU) (Example 5 of Chappelow, U.S. Published Patent Application No. 2007/0072954)

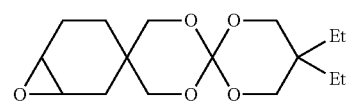

3,9-Diethyl-3,9-bis(3-trimethylsilylpropyloxymethyl)-1,5,7,1'-tetraoxaspiro[5.5]undecane (DEBTMSPOM-1,5,7,11-TOSU) (Example 6 of Chappelow, U.S. Published Patent Application No. 2007/0072954)

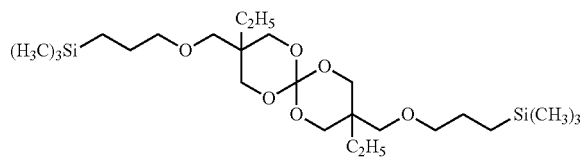

(9-Allyloxymethyl-9-ethyl-1,5,7,11-tetraoxaspero[5.5]undec-3-ylmethyl)-dimethylphenyl-silane (AOME-TOSU-MDMPS)

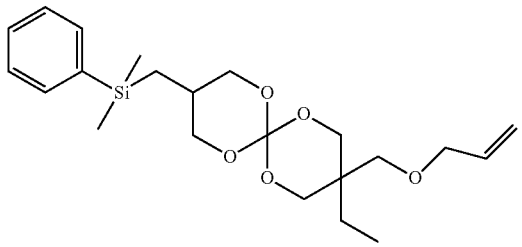 [SMILES: C=CCOCC1(CC)COC2(OCC(C[Si](C)(C)c3ccccc3)CO2)OC1]

Methyl[2-(7-oxabicyclo[4.1.0]hept-3-yl)ethyl]-phenyl[3-(3,9,9-triethyl-1,5,7,1'-tetraoxaspiro[5.5]undec-3-yl-methoxy)propyl]silane (MOB-HEP-TETOSU-MOPS)

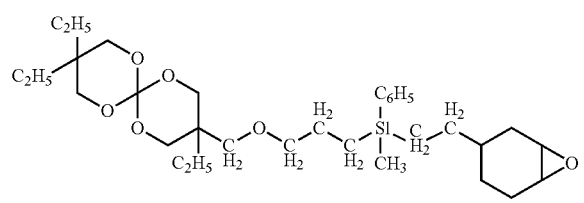

For biomaterial compositions containing fillers, stress-reducing monomers like TOSUs may be used for surface modification through the attachment of a surface-reactive ligand group, such as a pendant silyl or phosphate, that is reactive with the filler oxide surface. The organic moiety provides wetting and dispersion, interfacial (cure) reactivity, and interfacial strength properties while adding the potential to reduce internal stress in the composite. Since group length has a direct effect on interfacial bond and thus composite strength, the tether length between the reactive group and the surface active ligand is one design aspect may be considered. See Wang et al., Dharani L R. *Effect of interfacial mobility on flexural strength and fracture toughness of glass/epoxy laminates*, Journal of Materials Science 34(19) 4873-4882 (1999); Schuman et al., *Surface modified nanoparticles as enhanced fillers for dental polymer-particle composites*, J Dent Res 89 (2010); Schuman et al., *Improved dielectric breakdown strength of covalently-bonded polymer-particle nanocomposites*, Composite Interfaces, 17, 719-731 (2010). For example, for {3-(9,9-diethyl,1,5,7,11-tetraoxa-spiro(5.5) undec-3-yl)propyl}-trimethoxy-silane ("3TOSU"), a surface group density of about 26 Å2/group was obtained in reacting with glass particles or alumina nanorods, measured through TGA and also observed through XPS. Thus, addition of TOSUs (or compounds having analogous ring systems like the compounds shown below) to the silorane and/or as filler particle surface treatment should improve the mechanical properties of the silorane composite. The synthesis of (9,9-diethyl-1,5,7,11-tetraoxaspiro[5.5]undecan-3-yl)methyl)trimethoxysilane ("1TOSU") and (3-(9,9-diethyl-1,5,7,11-tetraoxaspiro[5.5]undecan-3-yl)propyl)trimethoxysilane ("3TOSU") is shown in the schemes below.

Scheme 1: Synthesis of 1-TOSU

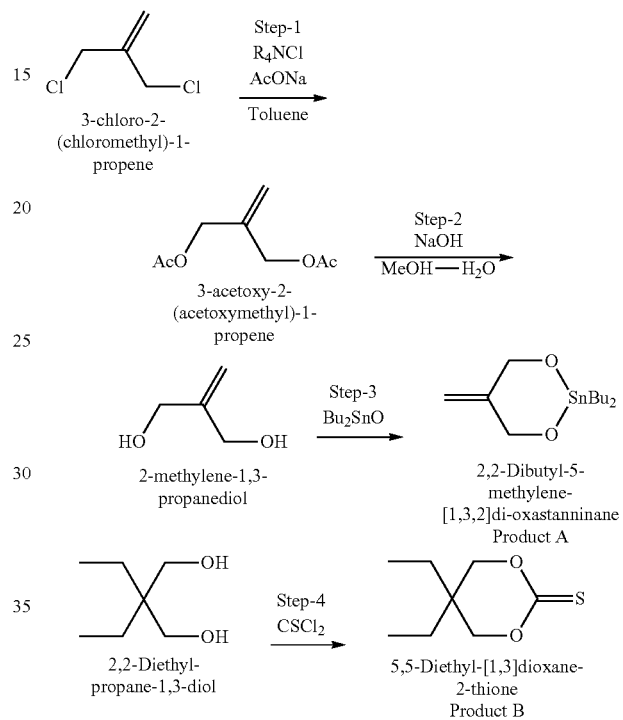

Scheme 2: Synthesis of 3-TOSU

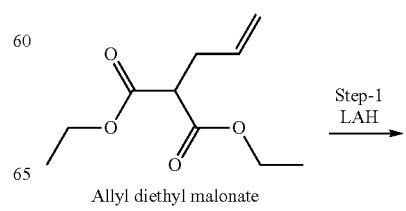

Allyl diethyl malonate

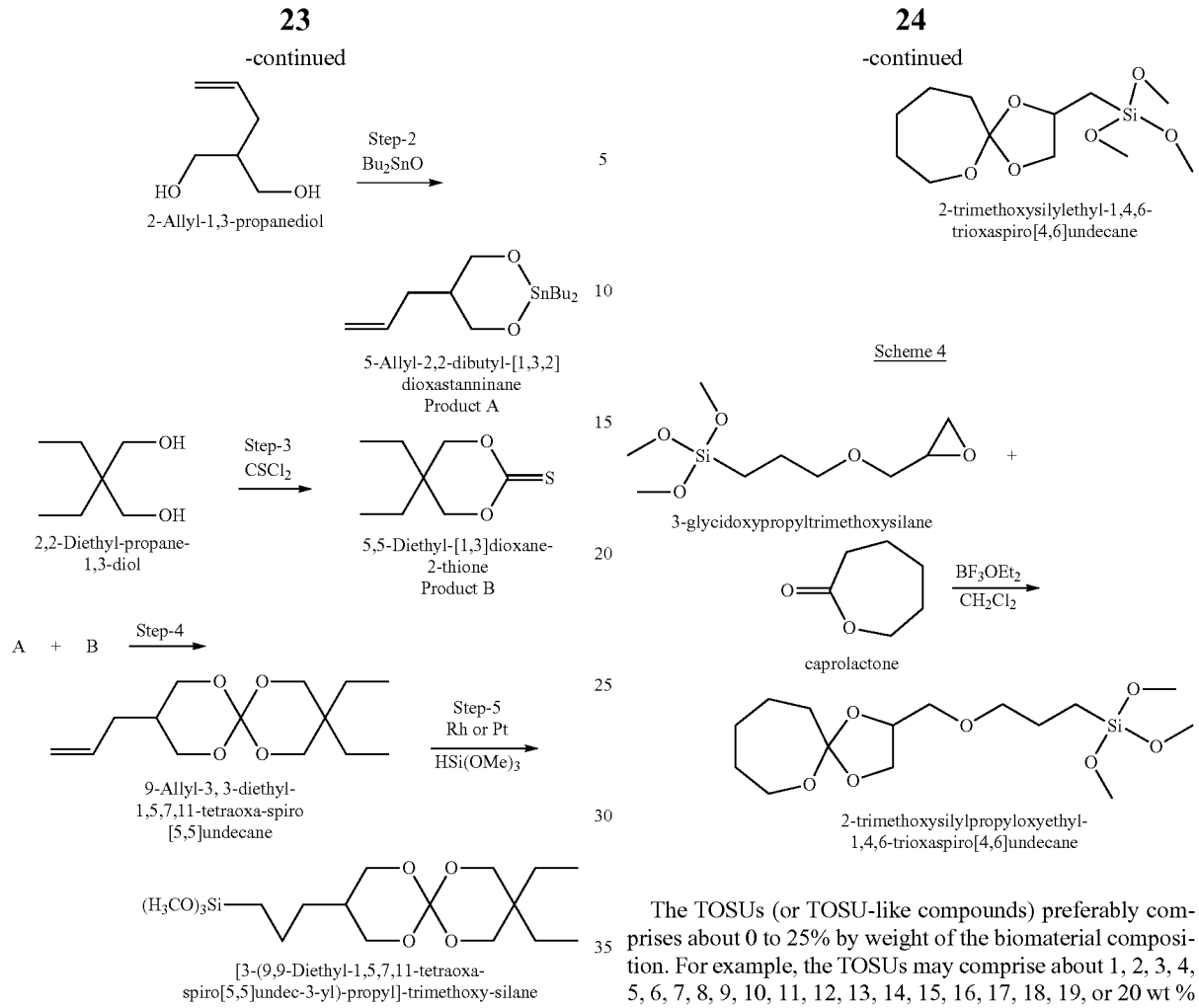

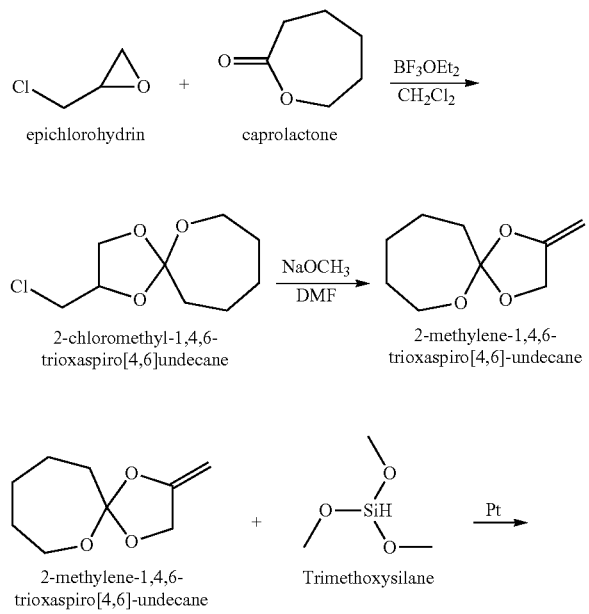

Scheme 3: Non-TOSU monomers of similar reactivity and properties as TOSU

The TOSUs (or TOSU-like compounds) preferably comprises about 0 to 25% by weight of the biomaterial composition. For example, the TOSUs may comprise about 1, 2, 3, 4, 5, 6, 7, 8, 9, 10, 11, 12, 13, 14, 15, 16, 17, 18, 19, or 20 wt % (or some range therebetween) of the biomaterial composition.

In another aspect, filler(s) are combined with one or more TOSUs. The optional filler and optional TOSU is preferably selected from the group consisting of (1) crushed light initiated SilMix (pre-polymerized SilMix); (2) DY5-yttria alumino-silicate; 15.0 wt % $Y_2O_3$, 5.0 wt % $Al_2O_3$, and 80 wt % $SiO_2$; (3) DY5 modified with 2-(3,4-epoxycyclohexyl)-ethyl-trimethoxysilane (ECHE); (4) DY5 modified with 3-(glycidyloxy)-propyl-trimethoxysilane (GPS); (5) DY5 modified with 3TOSU (3-(9,9-diethyl-1,5,7,11-tetraoxaspiro[5.5]undecan-3-yl)propyl)trimethoxysilane; (6) DY5 modified with 1TOSU ((9,9-diethyl-1,5,7,1'-tetraoxaspiro[5.5]undecan-3 yl)methyl)trimethoxysilane; (7) M12-barium boroaluminosilicate; 54.5 wt % $SiO_2$, 5.9 wt % $Al_2O_3$, 10.5 wt % $B_2O_3$, and 29.1 wt % BaO; (8) M12 modified with ECHE ethylcyclohexylepoxide; (9) M12 modified with 3TOSU (3-(9,9-diethyl-1,5,7,11-tetraoxaspiro[5.5]undecan-3-yl)propyl)trimethoxysilane; (10) M12 modified with 1TOSU ((9,9-diethyl-1,5,7,11-tetraoxaspiro[5.5]undecan-3yl)methyl) trimethoxysilane; (11) clays, montmorillonite plates of aspect ratio between about 100 to 300, surface modified with organic ammonium ions containing epoxy, hydroxyl, ether, ester, phosphate, allyl or vinyl functional groups, or silanes (trichloro, trimethoxy, triethoxy, dichloromethyl, dimethoxymethyl, diethoxymethyl, chlorodimethyl, methoxydimethyl, or ethoxydimethyl) containing a pendant epoxy, hydroxyl, ether, ester, phosphate, allyl or vinyl functional group; and (12) nanoparticles as spherical, nanofiber, nanowhisker, or nanorod—especially gamma aluminum, hydroxyapatite, calcium phosphate, zirconium, or titanium, with aspect ratio in the range of about 1 to 200, preferably between 1 and 20, neat or surface modified with organosilanes (trichloro, trimethoxy, triethoxy, dichloromethyl, dimethoxymethyl, diethoxymethyl, chlorodimethyl, methoxydimethyl, or ethoxydimethyl) containing a pendant epoxy, hydroxyl, ether, ester, phosphate, allyl or vinyl functional group or surface modified with organophosphates containing a pendant epoxy, hydroxyl, ether, ester, allyl or vinyl functional group, including 1TOSU, 3TOSU, or a TOSU-phosphate surface active, ligand groups.

The following examples are offered to aid in understanding the invention and are not to be construed as limiting the scope thereof.

EXAMPLE 1

Preparation of Exemplary Bone Cement Compositions

In this example, various biomaterials useful as bone cement compositions were prepared. All samples were prepared at room temperature (about 20° C.) under yellow light (for the light-initiated systems and the dual chemical/light curing systems, but not the chemical curing systems) in order to prevent premature polymerization. The samples will be referred to as either neat resins (no filler) or filled resin (may include one or more fillers).

Each of the bone cement compositions comprised two silorane monomers, bis[2-(3{7-oxabicyclo[4.1.0]heptyl}) ethyl]methylphenyl silane (PHEPSI) and 2,4,6,8-tetrakis(2-(7-oxabicyclo[4.1.0]heptan-3-yl)ethyl)-2,4,6,8-tetramethyl-1,3,5,7,2,4,6,8-tetraoxatetra-silocane (CYGEP). Both PHEPSI and CYGEP were prepared using adapted procedures and used at purities greater than 95.8% as determined by $^1$H NMR spectroscopy. See Aoki, U.S. Pat. No. 6,255,428; Crivello, *The Synthesis and Cationic Polymerization of Multifunctional Silicon-Containing Epoxy Monomers and Oligomers*, J. Polym. Sci. Part A: Polym. Chem. 32 683-697 (1994). P1 comprises a chemical cure system comprising an organometallic catalyst and an accelerator. P2 comprises a dual chemical/light cure system comprising and organometallic catalyst and a photoinitiation system.

P1 comprises (A) co-monomer system SilMix (1:1 by weight of PHEPSI and CYGEP), between about 40 to 55 wt %; (B) photoacid p-(octyloxyphenyl)phenyliodonium hexafluoroantimonate, between about 0.05 to 0.20 wt %; (C) Lamoreaux's catalyst, between about 0.09 to 0.2 wt %; (D) filler DY5, between about 10 to 20 wt %; and (E) filler crushed SilMix, between about 25 to 50 wt %. The following table includes several exemplary bone cement compositions that were prepared.

TABLE 3

Exemplary P1 formulations

| SilMix Silorane Co-Monomer | Pre-polymerized SilMix | DY5 | PIH | LMC |
|---|---|---|---|---|
| 0.5466 | 0.3500 | 0.1000 | 0.0014 | 0.0020 |
| 0.4000 | 0.4500 | 0.1472 | 0.0008 | 0.0020 |
| 0.4000 | 0.4500 | 0.1472 | 0.0008 | 0.0020 |
| 0.4000 | 0.3960 | 0.2000 | 0.0020 | 0.0020 |
| 0.4722 | 0.3997 | 0.1247 | 0.0017 | 0.0017 |
| 0.4242 | 0.4118 | 0.1618 | 0.0011 | 0.0011 |
| 0.4472 | 0.3500 | 0.2000 | 0.0020 | 0.0008 |
| 0.4000 | 0.3960 | 0.2000 | 0.0020 | 0.0020 |
| 0.4000 | 0.4500 | 0.1472 | 0.0020 | 0.0008 |

TABLE 3-continued

Exemplary P1 formulations

| SilMix Silorane Co-Monomer | Pre-polymerized SilMix | DY5 | PIH | LMC |
|---|---|---|---|---|
| 0.5472 | 0.3500 | 0.1000 | 0.0020 | 0.0008 |
| 0.4972 | 0.4000 | 0.1000 | 0.0008 | 0.0020 |
| 0.5478 | 0.3500 | 0.1000 | 0.0008 | 0.0014 |
| 0.4483 | 0.3994 | 0.1494 | 0.0014 | 0.0014 |
| 0.4000 | 0.3984 | 0.2000 | 0.0008 | 0.0008 |
| 0.4483 | 0.3994 | 0.1494 | 0.0014 | 0.0014 |
| 0.4472 | 0.3500 | 0.2000 | 0.0020 | 0.0008 |
| 0.4960 | 0.3500 | 0.1500 | 0.0020 | 0.0020 |
| 0.4472 | 0.3500 | 0.2000 | 0.0008 | 0.0020 |
| 0.5466 | 0.3500 | 0.1000 | 0.0014 | 0.0020 |
| 0.4483 | 0.3994 | 0.1494 | 0.0014 | 0.0014 |
| 0.4483 | 0.3994 | 0.1494 | 0.0014 | 0.0014 |
| 0.4460 | 0.4500 | 0.1000 | 0.0020 | 0.0020 |
| 0.4000 | 0.4500 | 0.1472 | 0.0020 | 0.0008 |
| 0.4978 | 0.3747 | 0.1247 | 0.0017 | 0.0011 |
| 0.4484 | 0.4500 | 0.1000 | 0.0008 | 0.0008 |
| 0.5478 | 0.3500 | 0.1000 | 0.0008 | 0.0014 |
| 0.4475 | 0.4247 | 0.1247 | 0.0017 | 0.0014 |
| 0.4000 | 0.3984 | 0.2000 | 0.0008 | 0.0008 |
| 0.4984 | 0.3500 | 0.1500 | 0.0008 | 0.0008 |
| 0.5472 | 0.3500 | 0.1000 | 0.0020 | 0.0008 |
| 0.4472 | 0.3500 | 0.2000 | 0.0008 | 0.0020 |
| 0.4000 | 0.3960 | 0.2000 | 0.0020 | 0.0020 |
| 0.4460 | 0.4500 | 0.1000 | 0.0020 | 0.0020 |
| 0.4722 | 0.3747 | 0.1497 | 0.0017 | 0.0017 |
| 0.4483 | 0.3994 | 0.1494 | 0.0014 | 0.0014 |
| 0.4984 | 0.3500 | 0.1500 | 0.0008 | 0.0008 |
| 0.4484 | 0.4500 | 0.1000 | 0.0008 | 0.0008 |
| 0.4960 | 0.3500 | 0.1500 | 0.0020 | 0.0020 |
| 0.4484 | 0.3747 | 0.1747 | 0.0011 | 0.0011 |
| 0.4972 | 0.4000 | 0.1000 | 0.0008 | 0.0020 |

P2_DY5_mod_ECHE ("P2A") comprises (A) co-monomer system SilMix (1:1 by weight of PHEPSI and CYGEP), between about 35 to 55 wt %, %; (B) Lamoreaux's catalyst, between about 0.3 to 0.8 wt %; (C) a light initiation system comprising about 3.0 wt % p-(octyloxyphenyl)phenyliodonium hexafluoroantimonate, about 1.0 wt % camphorquinone, and about 0.15 wt % ethyl 4-dimethylaminobenzoate; and (D) a filler ECHE modified DY5, between about 45 to 65 wt %.

P2_DY5_mod_3TOSU ("P2B") comprises (A) co-monomer system SilMix (1:1 by wt of PHEPSI and CYGEP), between about 35 to 55 wt %; (B) Lamoreaux's catalyst, between about 0.3 to 0.8 wt %; (C) a light initiation system comprising about 3.0 wt % p-(octyloxyphenyl)phenyliodonium hexafluoroantimonate, about 1.0 wt % camphorquinone, and about 0.15 wt % ethyl 4-dimethylaminobenzoate; and (D) a filler 3TOSU modified DY5, between about 45 to 65 wt %.

P2_DY5_mod_1TOSU ("P2C") comprises (A) co-monomer system SilMix (1:1 by wt of PHEPSI and CYGEP), between about 35 to 55 wt %; (B) Lamoreaux's catalyst, between about 0.3 to 0.8 wt %; (C) a light-initiation system comprising about 3.0 wt % p-(octyloxyphenyl)phenyliodonium hexafluoroantimonate, about 1.0 wt % camphorquinone, and about 0.15 wt % ethyl 4-dimethylaminobenzoate; and (D) a filler 1TOSU modified DY5, between about 45 to 65 wt %.

The components of the exemplary inventive formulations are mixed together in order to indicate polymerization. In a preferred aspect, all of the components except the Lamoreaux's catalyst are first mixed together in a suitable mixing device (such as a mixing cup). The desired amount of Lamoreaux's catalyst is added and then the combined mixture is further mixed.

For comparative purposes, in some instances, the inventive formulations were compared to those of conventional PMMA-based Simplex P Bone Cement (Stryker Homedica Osteonics). The first powder component is a mixture of polymethyl methacrylate (PMMA) (15.0%), methyl methacrylate-styrene-copolymer (75.0%), and barium sulfate (10.0%). The second component of Simplex P bone cement is a liquid monomer containing methyl methacrylate monomer (97.4%), N,N-dimethyl-p-toluidine (2.6%) and hydroquinone (7515 ppm). The two components are mixed at a ratio of 2 g powder to 1 mL liquid monomer to initiate the free-radical polymerization process.

EXAMPLE 2

Mechanical Testing

Polymerization Stress

The bone cement compositions of the present invention will be tested for polymerization stress. Two glass rods are placed 1 mm apart on the Bose mechanical testing instrument. Strain during testing will be held constant, less than 1.0 μm deflection, during polymerization. The peak load during polymerization will be used to calculate polymerization stress as generally described in Eick et al., *Properties of silorane-based dental resins and composites containing a stress-reducing monomer*, Dent Mater 23(8) 1011-1017 (2007), which is incorporated by reference.

Maximum Exotherm Temperature

Exotherm temperature was measured using a K-type thermocouple (Omega, Stamford, Conn.) affixed to a glass slide and slightly bent so that the tip of the thermocouple was positioned in the center of an acetal resin (Delrin®) washer (McMaster-Carr, Aurora, Ohio), which was also affixed to the glass slide with lab tape. Each composite formulation (0.6 g) was mounded to completely cover the tip of the thermocouple. The sample was then irradiated (12 mm diameter tip, 450 mW/cm$^2$ (Cure Rite, Dentsply Caulk, Milford, Del.) at a distance of 3 mm) using a dental curing lamp (3M XL3000, St. Paul, Minn.) for two minutes. Specimens were inspected after testing, and results were excluded from further study if the tip contacted the glass slide or was not entirely covered with the composite. Temperature data were recorded using a data logger (OM-PLTC, Stamford, Conn.) at 1 Hz for 30 minutes post-irradiation. Handling time was defined as the time between initiation and when the exotherm reached half of its peak temperature.

Handling Properties/Handling Time

The handling properties generally refer to the time from addition of catalyst or irradiation until one cannot manipulate the material. That is, handling time refers to the length of time the material can be manipulated between mixing and polymerization to allow for placement in the body. Bone cement consistently reaches dough time around 1.9 mm penetration (about 9 minutes post-mixing). Curing time occurs when penetration is 0.0 mm (about 15 minutes).

Handling properties will be measured with a penetrometer. Timing will start as the monomer (0.75 g) is mixed and placed in an aluminum washer (12.7 mm diameter, 2.5 mm deep). Penetration measurements (mm) will be taken periodically with a mass of 49.2 g applied to the penetrometer cone for 5 seconds. This test will provide viscosity, and curing, dough, and manipulation time.

Flexural Strength and Modulus

The bone cement compositions of the present invention will be tested for flexural strength. Flexural specimens (25 mm×2 mm×2 mm) were formed in borosilicate glass tubes (VitroCom, Mountain Lakes, N.J.) coated with silicone spray mold release (Mark V Laboratory, East Granby, Conn.) as per ISO specification 4049. A pipette was used to fill the molds with resin. The specimen was irradiated (12 mm diameter tip, 450 mW/cm$^2$ (Cure Rite, Dentsply Caulk, Milford, Del.) at a distance of 3 mm) using a dental curing lamp (XL3000; 3M, St. Paul, Minn.) for two minutes along the top surface at three consecutive regions for 40 seconds each, 40 seconds in a scanning motion along the bottom of the glass mold, and then the specimen was removed from the glass. The method of photoinitiating specimens and induction of any overlapping regions have been shown to not have an effect on flexural properties. The specimens were stored in phosphate buffered saline (PBS), at 23±1° C., for 24 hours, after which, the specimen was loaded, until fracture, at a displacement rate of 3.7 mm/min in a four-point bend fixture with a support span of 20 mm on a BOSE mechanical tester (EnduraTEC ELF 3300, Eden Prairie, Minn.). Specimens with visible surface flaws, bubbles, or undistributed filler particles were excluded from the study. The resulting stress-strain curve was used to determine flexural strength ($\sigma_B$) and flexural modulus of elasticity ($E_B$). The following two equations were used to calculate stress (Eq 1) and strain (Eq 2). The resulting stress-strain curve was used to determine flexural yield strength and flexural modulus of elasticity $$\sigma = \frac{\text{load} \times \text{load span}}{\text{specimen width} \times (\text{specimen thickness})^2}$$

$$\varepsilon = \frac{5.4 \times \text{displacement} \times \text{specimen thickness}}{\text{load span}^2}$$

Compressive Strength

The bone cement compositions of the present invention will be tested for compressive strength. Cylindrical specimens (6 mm diameter×12 mm height) were formed in a metal mold coated with silicone spray mold release as per ISO specification 4049. A pipette was used to fill the mold and composite formulations were either light-irradiated for 2 minutes at each end of the cylinder for photoinitiated materials, or allowed to polymerize for 30 minutes for chemically initiated materials. The cylinders were then removed from the molds and stored in PBS, at 23+/−1° C., for 24 hours, after which specimens were loaded until fracture at a displacement rate of 20 mm/min between two smooth platens in compression. Specimens with visible surface flaws, bubbles, or undistributed filler particles were excluded from the study. The resulting peak load prior to failure was used to calculate compressive strength.

TABLE 4

Range of properties for P1 and P2 (P2A, P2B, P2C).

| | P1 | P2 | Desired properties | ISO 5833 Standard |
|---|---|---|---|---|
| Polymerization stress (MPa) | — | — | ≤1.0 | |
| Exothermicity (° C.) | 25-30 | 26 ± 0.5 | ≤45 | ≤90 |
| Handling time (mins) | 8-10 | 8-10 | ≤20 | 3-15 |
| Intrusion (mm) | — | — | | ≥2 |
| Flexural modulus (GPa) | 1.5-1.7 | 2.2-3.5 | | ≥1.8 |
| Flexural strength (MPa) | 22-33 | 25-60 | | ≥50 |
| Compressive strength (MPa) | — | 68-77 | | ≥70 |
| Cytotoxicity (% cell death) | 17% | — | ≤20% | |

EXAMPLE 3

Cytotoxicity on Neat Dual Cure SilMix

In this example, the objective was to determine the bone cell growth on chemically cured silorane resins using a polymerization system containing acetic acid as a proton donor plus exposure to halogen lamp. The compositions are described in Table 5. Solid resin discs (9 mm diam×0.5 mm thick) (n=12) were yellow and transparent. Discs passed the GNT and were delivered in a closed plastic container. The discs were yellowish transparent and were used as received (no UV light sterilization as in previous experiments). Discs were placed into 48-well plate (n=4), pre-washed in growth media for 1 h at 35° C./5% $CO_2$. Then the wash media was replaced with 0.5 mL MLO-A5 cell suspension containing $2 \times 10^4$ cells. After 24 hours and 48 hours in culture, cell viability was measured using the MTT assay and the number of live and dead cells was measured using the TBE assay. The results are summarized in Table 6 and FIG. 1.

TABLE 5

Dual Chemical/Light Cured Silorane Resins Formulation Compared to Light Cured Silorane

| Chem ID | Bio ID | SilMix | AA | PIH | CPQ | EDMAB |
|---|---|---|---|---|---|---|
| SM17-DV-A | DCA | 3 g | 0.024 g | 0.024 g | 0.008 g | 0 g |
| SM17-DV-B | DCB | 3 g | 0.048 g | 0.048 g | 0.016 g | 0 g |
| SM17-DV-C | DCC | 3 g | 0.096 g | 0.096 g | 0.032 g | 0 g |
| SM17 PIH B | Light initiated used as control | 3 g | 0 g | 0.094 g | 0.031 g | 0.005 g |

AA = acetic acid; PIH = p-(octyloxyphenyl)phenyliodonium hexafluoroantimonate; CPQ = camphorquinone; EDMAB = ethyl p-dimethylaminobenzoate.

TABLE 6

Live and Dead Cell Numbers and Calculated Percent in the Trypan Blue Test.

| | 24 h live cells | | 24 h dead cells | | 48 h live cells | | 48 h dead cells | |
|---|---|---|---|---|---|---|---|---|
| ID | # cells × $10^4$ | % | # cells × $10^4$ | % | # cells × $10^4$ | % | # cells × $10^4$ | % |
| control | 26 ± 1 | 89 | 3 ± 1 | 11 | 51 ± 9 | 89 | 6 ± 2 | 11 |
| DCA | 4 ± 3 | 43 | 5 ± 2 | 57 | 8 ± 2 | 65 | 3 ± 2 | 35 |
| DCB | 9 ± 3 | 68 | 4 ± 1 | 32 | 9 ± 3 | 66 | 5 ± 1 | 34 |
| DCC | 10 ± 3 | 75 | 3 ± 1 | 24 | 16 ± 4 | 81 | 4 ± 1 | 19 |
| PIH (light) | 15 ± 4 | 86 | 2 ± 0.5 | 14 | 24 ± 6 | 89 | 3 ± 1 | 10 |

The MTT results indicate that dual cured resins (DCB and DCC) produced adherent cell viability similar ($p>0.05$) to the photoinitiated silorane resin PIH in 24 hours (FIG. 1, panel e) and 48 hours (FIG. 1, panel f) cultures. However, in the Trypan blue assay (Table 6), only the dual cured resin DCC produced live cell numbers (adherent and non adherent) similar ($p>0.05$) with the photoinitiated silorane resin PIH in 24 hours (FIG. 1, panel a) and 48 hours (FIG. 1, panel b) cultures.

From the MIT and Trypan blue results, the dual cured resin DCC is more biocompatible than the others tested and was the most similar to the photoinitiated silorane PIH. Among the dual cured resins, the resin DCC contained more polymerization system (about 7%) than the other two resins (DCB 3.6% and DCA 1.8%) which used decreasing amounts of acetic acid (Table 5). It is thought that with more initiator there is likely more polymerization. Therefore, there would be less monomer and more reacted polymer resulting in less toxicity. However, since the dead cells (as number and percent) appear similar for all chemically cure resins, their decrease in cell numbers seem to be an effect of cell growth inhibition rather than cell death. Growth inhibition may have occurred because cells did not attach well to the polymer surfaces.

EXAMPLE 4

Cytotoxicity of Neat Chemically Initiated Silorane Using LMC

In this example, the Lamoreaux's catalyst-cured resin (SilMix CC) was tested for in vitro biocompatibility and was found to be comparable to the light cure silorane resin (SilMix LC). The formulations investigated are shown in the following Table 7.

TABLE 7

Chemically cured silorane (SilMix CC) formula compared to light cured silorane (SilMix LC)

| Polymer | PHEPSI/ CYGEP 1:1 (g) | LMC (g) | PIH (g) | CPQ (g) | EDMAB (g) |
|---|---|---|---|---|---|
| SilMix LC is control and light initiated | 3.00304 (95.85%) | | 0.09405 (3.005%) | 0.03130 (0.99%) | 0.00468 (0.153%) |
| SilMix CC | 4.00133 (99.89%) | 0.00274 (0.07%) | 0.000148 (0.04%) | | |

Figure 2:
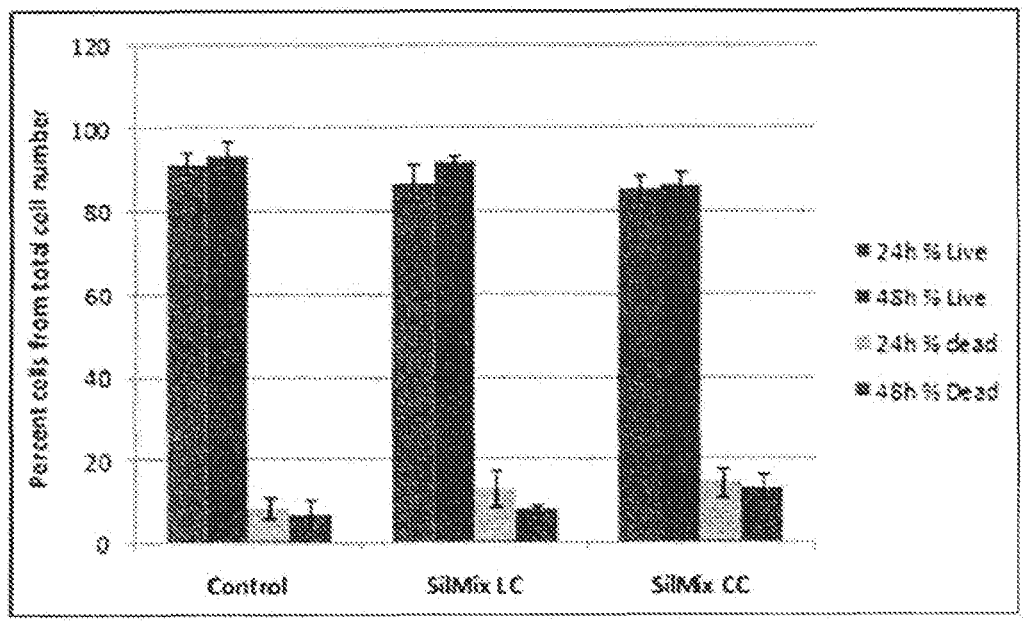
FIG. 2 shows that the in vitro biocompatibility of the chemical cure silorane resin (SilMix CC) is comparable to the light cure silorane resin (SilMix LC) as demonstrated by the similar number of live and dead adherent and non-adherent cells counted after 24 and 48 hours incubation with MLO-A5 cells.

LMC = Lamoreaux catalyst;
PIH = p-(octyloxyphenyl)phenyliodonium hexafluoroantimonate;
CPQ = camphorquinone;
EDMAB = ethyl p-dimethylaminobenzoate Polymer discs were prepared from both photoinitiated (LC) and chemically initiated (CC) SilMix. The samples were sterilized on the day of assay using two hour UV light exposure in a tissue culture laminar hood. Then, discs were placed into 48-well plate (n=3-4), pre-washed in growth media for one hour at 35° C./5% $CO_2$. The wash media was discarded and replaced with $2\times10^4$ MLO-A5 cells/0.5 mL. After 24 hours and 48 hours of incubation, cell viability and proliferation was measured using the trypan blue method. Another set of discs was used for extraction of leachables by incubating the discs for 24 hours in culture media with serum. After 24 hours, the extracts were transferred to a monolayer of MLO-A5 cells (seeded the day before). The cells were exposed to the extracts for 24 hours, after which the cell viability was measured using the MTT assay. Based on the trypan blue exclusion assay results, the number of live cells in the wells with the polymer SilMix LC and SilMix CC were less than (p<0.05) the control (plastic cell culture wells), while there was no significant difference in the number of dead cells. The percentage of live to dead cells with LC and CC SilMix was the same as the controls (FIG. 2) showing that the reduction in cell number was not due to toxicity but was due to reduced proliferation. This is most likely due to reduced adherence to the polymer surface as bone cells have been shown to require an attachment surface to proliferate. This lack of cytotoxicity was confirmed in the MTT assay. The Formazan product in the presence of extracts from SilMix LC (OD=0.954) and SilMix CC (0.96±3) were similar to the controls (0.92±5). From these results, it is clear that the in vitro cytocompatibility of the chemical cure SilMix is comparable to the photo-initiated SilMix in the 24 and 48 hour cultures with bone like MLO-A5 cells.

EXAMPLE 5

Stabilization of Fractured Excised Femur with Differently Cured SilMix Resin

In this example, the stabilization effects of a dual chemical/light cured composition of the present invention was compared to that of a conventional light curing system. A halogen light (100 W) at a distance of 18 inches was used to cure the system over a period of about 5 minutes. The dual cure system comprised (A) co-monomer system SilMix (1:1 by weight of PHEPSI and CYGEP), 93 wt %; (B) weak Bronstead acid—acetic acid, 3 wt %, (C) photoacid p-(octyloxyphenyl)phenyliodonium hexafluoroantimonate, 3 wt %, and (D) photosensitizer, camphorquinone 1 wt %. For comparative purposes, a light cure system comprising 95.85 wt % SilMix, 3 wt % PIH, 1 wt % camphorquinone, and 0.15 wt % EDMAB was used.

More specifically, in this example, functional studies have been developed to determine the ability of filled SilMix to stabilize bone in animal models. Pilot testing has begun on extracted and in vivo rat femurs with a clean-cut fracture introduced with a circular saw. SilMix or control bone cement is applied around the bone creating a 1-mm wide by 1-2 mm thick band of composite material. The flexural strength of the stabilized bones is then determined using four-point bend testing. These initial studies have revealed that the more elastic behavior of the SilMix is better suited to provide bone stability than the relatively brittle bone cement (Simplex® P).

Figure 3:
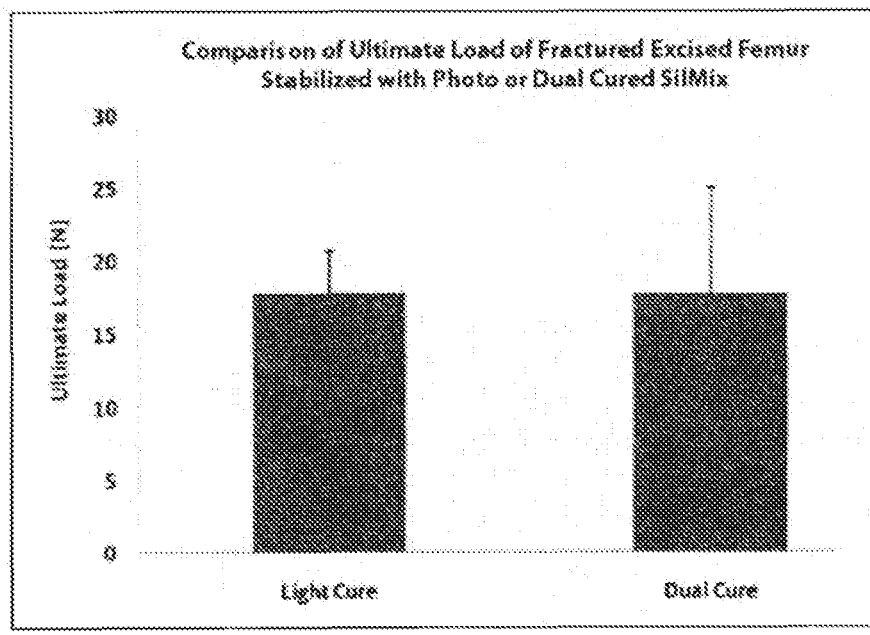
FIG. 3 shows that the ultimate load to fracture of excised mouse femora is similar when stabilized with either photo-initiated or dual chemical/light cured silorane resin.

Six mice were sacrificed by authorized personnel. The femora were then harvested from freshly sacrificed mice and stripped of soft tissues. Femora were fractured using a hand-held circular saw. The fractured bones were repositioned and stabilized with 50-70 μL of each SilMix resins around the fracture site (n=6/SilMix formulation). The resin was cured either using a halogen lamp for 5 minutes (dual initiation SilMix) or a dental curing lamp 3 times for 20 seconds (photoinitiated SilMix). The stabilized bones were stored in a humidified atmosphere for 24 hours, and then tested biomechanically. The data (FIG. 3) show that there is no difference between the photoinitiated and dual cured SilMix group.

EXAMPLE 6

Characterization of Flexure Strength and Modulus of Neat Bone Cement

Figure 4:
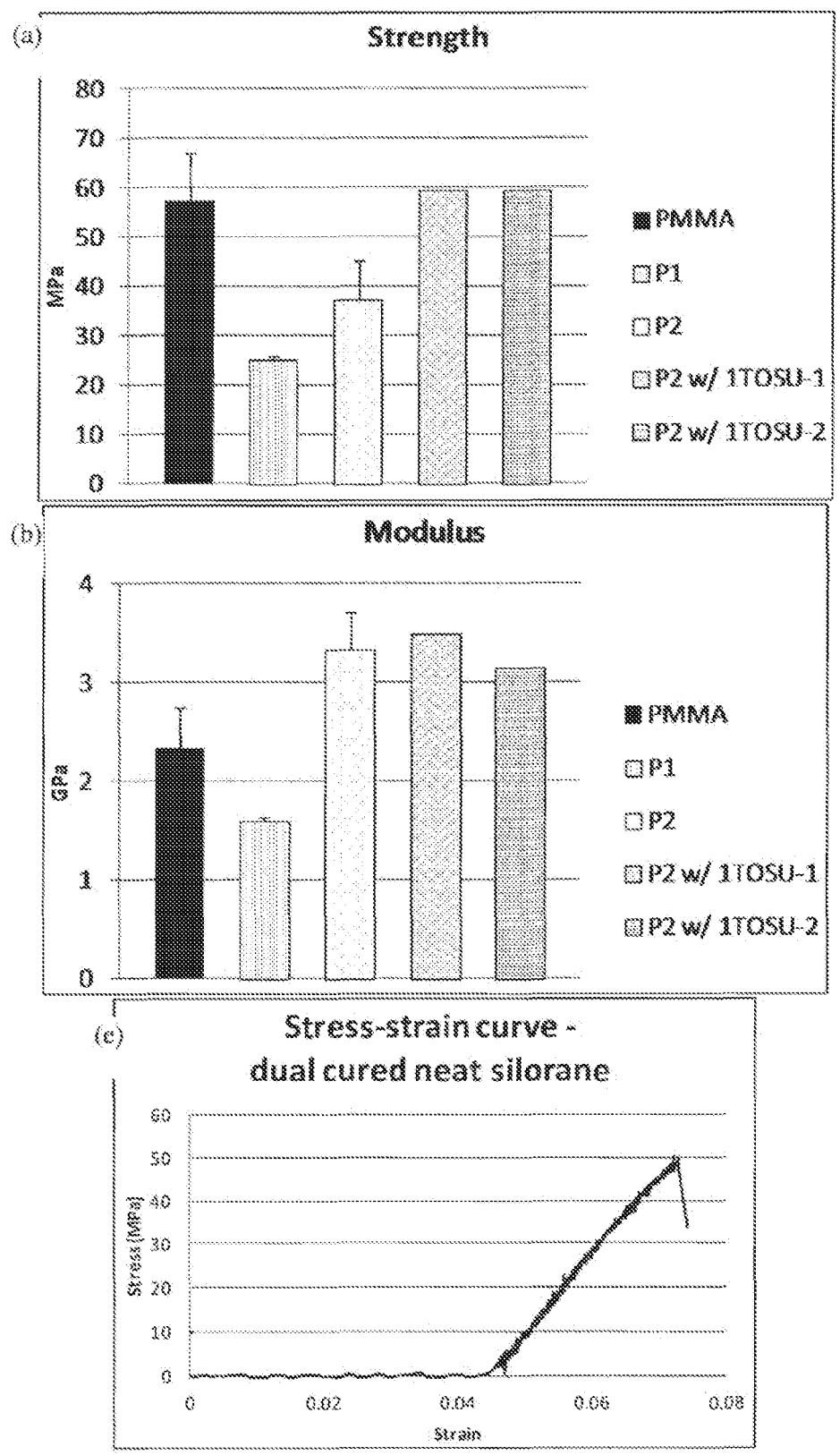
FIG. 4 shows the chemical and dual chemical/light cured silorane stress and modulus measurements. Panels a and b illustrate the flexural strength and flexural modulus of the P1 and P2 systems compared to conventional PMMA systems. Panels c and d illustrate the flexural strength and modulus of two exemplary P1 systems. Panel e illustrates the stress-strain curve for an exemplary neat dual chemical/light cured system comprising acetic acid, PIH, and camphorquinone.
Figure 4:
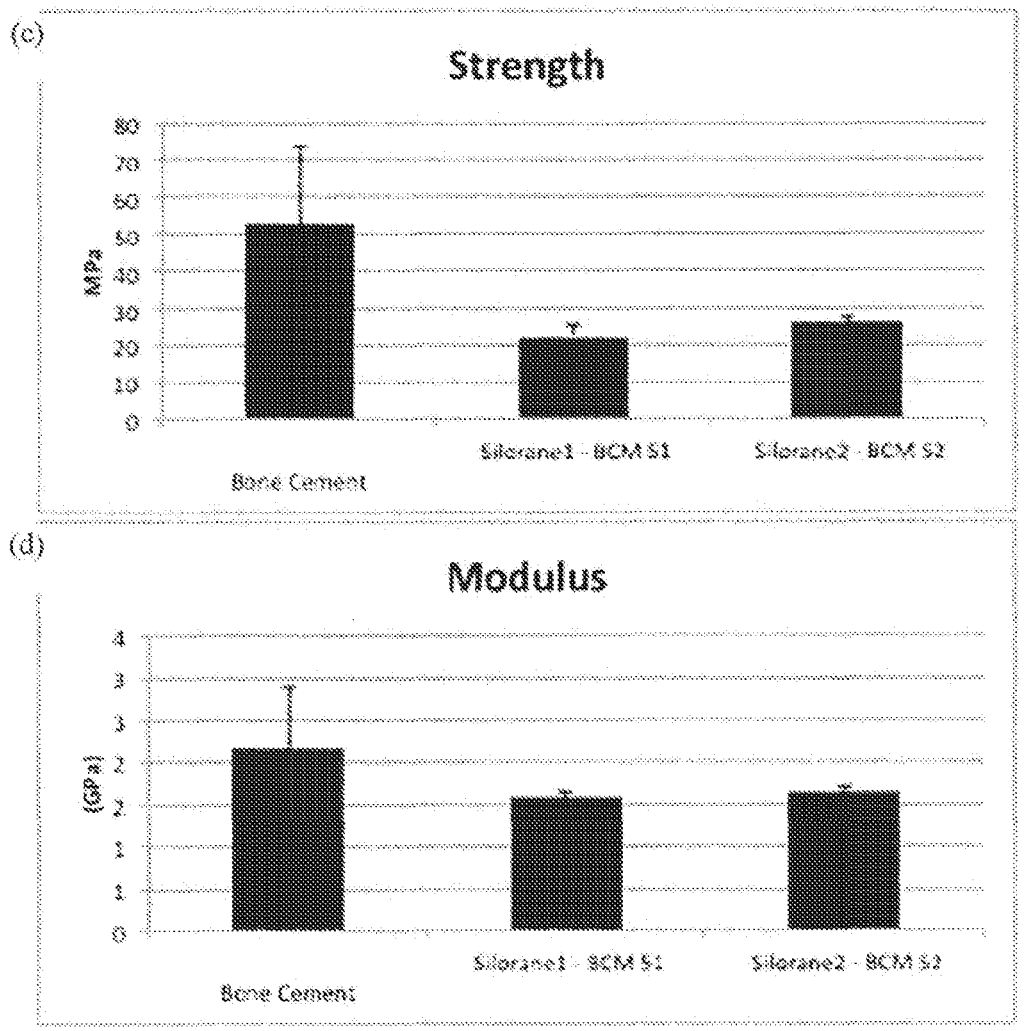

As discussed above, the flexural strength and flexural modulus results for the P1 system and P2 systems was investigated. The results are illustrated in panels a and b of FIG. 4. More specifically, panel a of FIG. 4 illustrates the flexural strength while panel b of FIG. 4 illustrates the flexural modulus of the P1 and P2 systems compared to a conventional PMMA system. P1 (aka BCM52) comprised 50 wt % SilMix, 0.1 wt % PIH, 0.1 wt % Lamoreaux's catalyst, 35.8 wt % pre-polymerized crushed SilMix, and 14 wt % DY5 filler. P2 comprised 39.45 wt % SilMix with a light initiation system (EDMAB 0.15 wt %; CQ 1 wt %; PIH; 3 wt %; SilMix 95.85 wt %), 0.56 wt % Lamoreaux's catalyst, and 59.99 wt % 3TOSU modified DY5 filler. "P2 w/1TOSU-1" and "P2 w/1TOSU-2" were two separate beams comprising 39.7 wt % SilMix with a light initiation system (EDMAB 0.15 wt %; CQ 1 wt %; PIH, 3 wt %; SilMix 95.85 wt %), 0.3 wt % Lamoreaux's catalyst, and 60.01 wt % 1TOSU modified DY5 filler.

In separate experiments, the flexural strength and flexural modulus of two different P1-type of systems (Table 8) was investigated, the results of which are shown in FIG. 4 (panels c and d) and Table 9. It will be appreciated that these inventive systems are filled systems containing Lamoreaux's catalyst.

TABLE 8

Exemplary P1 Systems

| Sample | Total (g) | % SilMix | % PIH | % LMC | % Pre-Polymerized SilMix | % DY5 |
|---|---|---|---|---|---|---|
| BCM51 | 3.17682 | 42.18 | 0.10 | 0.10 | 45.85 | 11.77 |
| BCM52 | 2.67889 | 49.95 | 0.10 | 0.10 | 35.85 | 14.00 |

TABLE 9

Flexural Strength/Modulus of Exemplary P1 Systems

| samples | Flexural Test Strength (MPa) | | Modulus (GPa) | | n | Mold | Storage |
|---|---|---|---|---|---|---|---|
| | Mean | StDev | Mean | StDev | | | |
| BCM51 | 22.26 | 2.78 | 1.58 | 0.06 | 7 | glass | 24 hr/PBS |
| BCM52 | 25.77 | 1.53 | 1.63 | 0.07 | 7 | glass | 24 hr/PBS |

In this example, the stress-strain curve for a neat dual chemical/light cure system having acetic acid was also determined as generally shown in panel e of FIG. 4. The biomaterial composition comprised 93 wt % SilMix, 3 wt % acetic acid, 3 wt % PIH, and 1 wt % camphorquinone. The dual chemical/light cured silorane required about 5 minute's exposure to halogen light to polymerize. There was concern about the compatibility of the mechanical testing molds that were developed for chemical cured materials. The compression cylinders are 1.2 cm long and 5 minute halogen light exposure results in polymerization throughout the specimen.

Seven flexure beams were produced of a reasonable quality (still some small flaws, mostly toward ends of beam where not directly affecting flexural testing). After 24 hours of dark storage at room temperature, these were loaded at a rate of 3.7 mm/min as previously with bone cement.

TABLE 10

Flexural Strength - Dual Cured Silorane (unfilled).

| beam | strength (MPa) | strain | modulus (MPa) |
|---|---|---|---|
| 1 | 41.3 | 7.3% | 1693.7 |
| 2 | 50.4 | 8.1% | 1908.1 |
| 3 | 74.1 | 9.8% | 2222.9 |
| 4 | 57.5 | 8.3% | 1724.0 |
| 5 | 42.5 | 8.2% | 1417.6 |
| 6 | 55.6 | 6.7% | 2627.7 |
| 7 | 40.7 | 6.9% | 1626.8 |
| Mean | 51.7 | 7.9% | 1888.7 |

These values (Table 10) were comparable to previously tested bone cement values. However, bone cement gave a yield strength instead of maximum strength. The dual cured specimens show a brittle fracture (FIG. 4).

EXAMPLE 7

Exotherms of Neat Chemically Initiated SilMix (SM)

In this example, the chemically cured composition comprised (A) co-monomer system SilMix (1:1 by weight of PHEPSI and CYGEP), 99.89 wt %; (B) photoacid p-(octyloxyphenyl)phenyliodonium hexafluoroantimonate, 0.04 wt %, and (C) organometallic catalyst, Lamoreaux's catalyst, 0.07 wt %. As a control, the light initiated composition comprised (A) co-monomer system SilMix (1:1 by weight of PHEPSI and CYGEP), 95.85 wt %; and (B) light initiation system comprising 3.0 wt % p-(octyloxyphenyl)phenyliodonium hexafluoroantimonate, about 1.0 wt % camphorquinone, and about 0.15 wt % ethyl 4-dimethylaminobenzoate.

Figure 5:
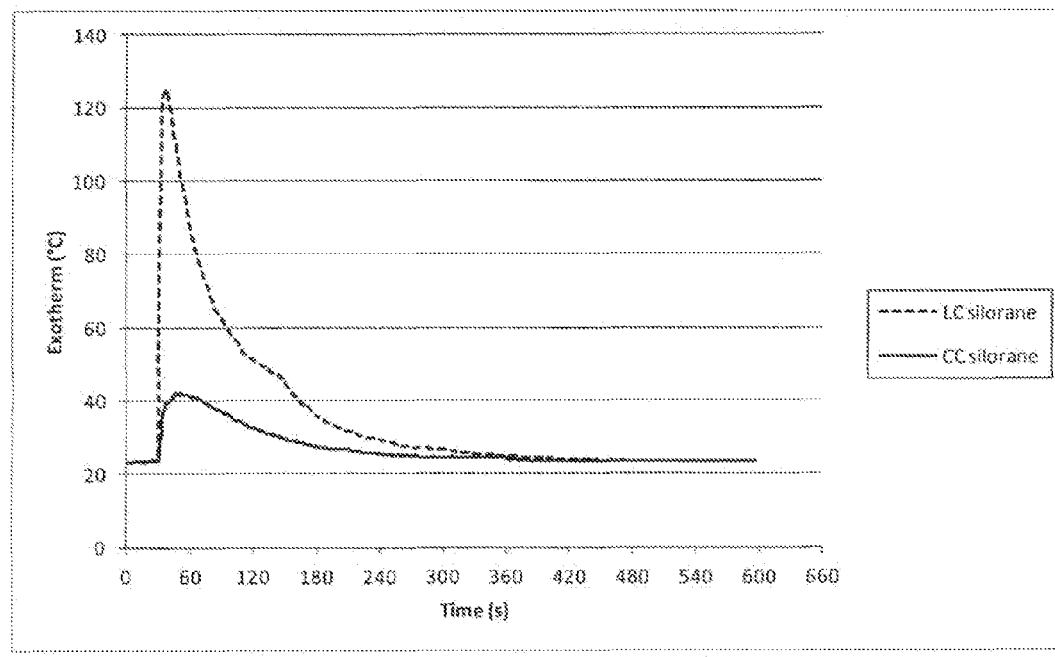
FIG. 5 shows the exotherm temperature data for photoinitiated and chemically initiated silorane resins. These results show that the photoinitiated silorane has a much higher exotherm (127° C.) than the chemically initiated (40° C.). The chemically initiated silorane also has a longer curing time. Note that the curing time presented for the chemical cure does not take into account the additional one minute of mixing.

Samples of approximately 120 mg were then placed on thermocouples. Thermocouples had been previously prepared by taping a delrin washer on a glass slide onto which the tip of the thermocouple was taped. The tip of the thermocouple was centered approximately in the delrin washer. Photoinitiated SM samples were also tested using a similar manner. However, after mixing samples were placed in the delrin washer/thermocouple set-up and irradiated for two minutes with a dental curing lamp. Peak exotherm was collected from the plots as well as cure time, defined as the time from mixing to pass peak exotherm to reach half or max temperature (Table 11). Sample temperature plots are shown in FIG. 5 for both the photo and chemical initiated SilMix.

TABLE 11

Maximum exotherm measurements for photoinitiated and chemically initiated silorane resins.

| | Peak Exotherm (° C.) | Cure time (s) | Repetitions (n) |
|---|---|---|---|
| Photoinitiated | 127.2 (6.2) | 51.4 (4.6) | 9 |
| Chemically | 31.1 (3.8) | 159.7 (70.4) | 6 |

It was also observed that the polymerization time and heat generated is directly proportion to the speed of mixing as well as of material. Thinner samples polymerize slower than larger samples. For example, 500 mg of material on glass slide polymerizes in 15 minutes (passes GNT); whereas, a 100 mg sample will take up to 45 minutes to polymerize. Also, the speed of mixing generates more heat and aids in the polymerization reaction. The LMC catalyst was mixed in by hand.

EXAMPLE 8

Filled Chemically Initiated Silorane Exotherm

Figure 6:
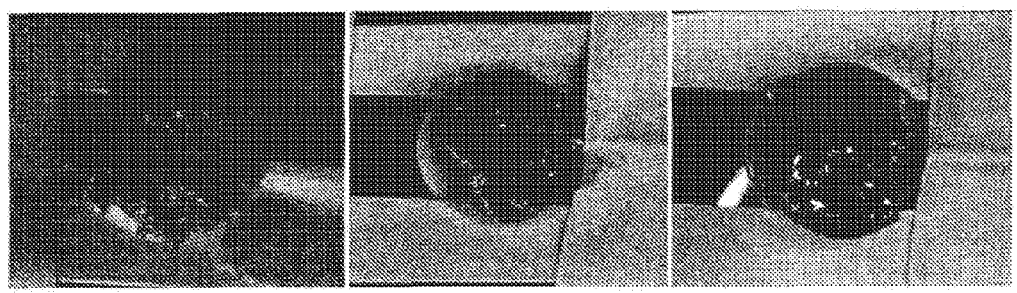
FIG. 6 is photographs of the silorane bone cement mimics. The first sample (BCM 1/2) did not mix well and formed a gritty clump of material. However, samples BCM 3/4 and BCM 5/6 were much smoother and polymerized with a glossy finish.

In this example, two formulations were tested (Table 12, FIG. 6). Bone cement mimics (BCM) 1/2 and 3/4 had the same composition but were derived from different batches of formulation. Bone cement mimic 5/6 contained a lower amount of PIH and LMC. Due to the thinness of the samples, it took approximately 30 minutes to complete cure to hardness (pass the one-1b GNT).

TABLE 12

Cure time of three silorane bone cement mimic formulations.

| Sample | % SM | % PIH | % LMC | % CSM | % DY5 | Max (° C.) | Curing Time (sec) |
|---|---|---|---|---|---|---|---|
| BCM 1 | 34.25 | 0.15 | 0.15 | 55.84 | 9.61 | 34.9 | 128 |
| BCM 2 | 34.25 | 0.15 | 0.15 | 55.84 | 9.61 | 35.3 | 156 |
| BCM 3 | 34.25 | 0.15 | 0.15 | 55.84 | 9.61 | 29.5 | 247 |
| BCM 4 | 34.25 | 0.15 | 0.15 | 55.84 | 9.61 | 32.7 | 243 |
| BCM 5 | 34.27 | 0.10 | 0.11 | 55.91 | 9.61 | 27.0 | 88 |
| BCM 6 | 34.27 | 0.10 | 0.11 | 55.91 | 9.61 | 27.0 | 96 |

SM—SilMix; PIH—phenyl iodonium salt; LMC—Lamoreaux's catalyst; CSM—crushed SM (polymerized); DY5—yttrium silicate glass filler (unmodified)

Figure 7:
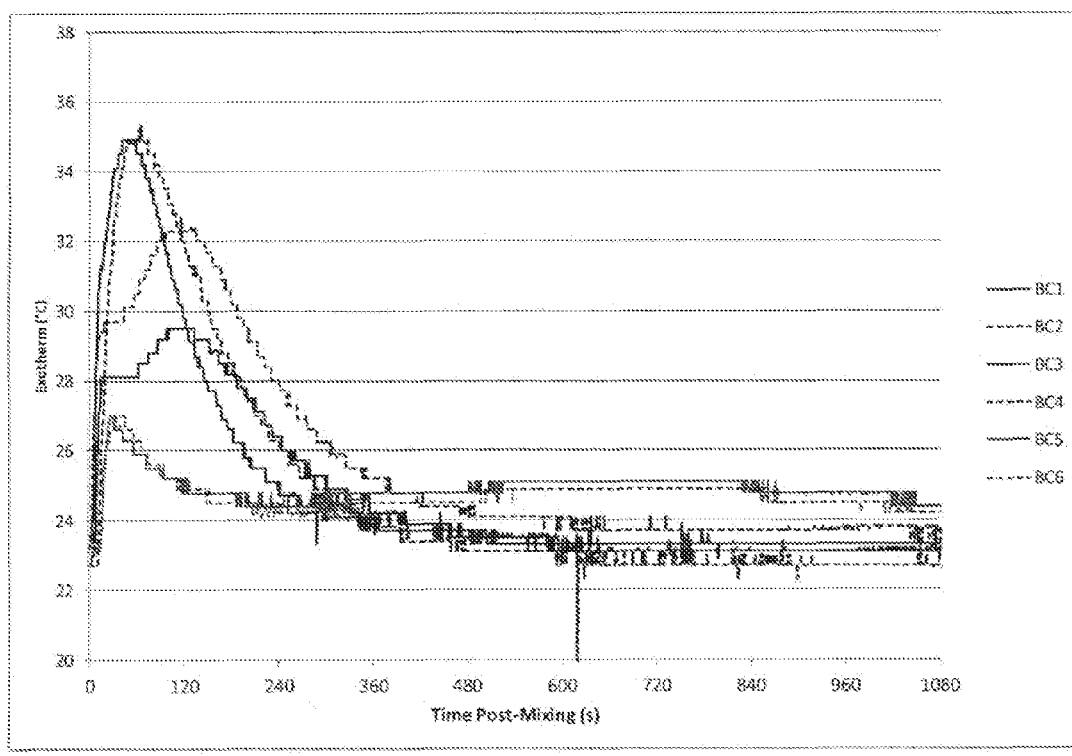
FIG. 7 is an exotherm profile of six exemplary biomaterial compositions in accordance with the present invention.

Overall, exotherm temperatures of the chemically cured silorane bone cement mimics were well below 45° C. limit (FIG. 7). There was some variability, likely due to difference in mixing techniques, time to add the LMC, etc. Lower concentrations of LMC catalyst resulted in a lower peak exotherm and somewhat of a double peak in temperature. These results were repeated, but only with two samples. Due to the narrow range in temperatures (about 10° C.), the resolution of our current thermocouple is inadequate (resulting in digitized plots). Need to identify alternate temperature recording device (RTD, thermistor, etc.) with greater resolution.

PROPHETIC EXAMPLE

It will be appreciated that biocompatibility is an important property for any biomaterial compositions of the present invention. In addition to the MLO-A5 cell lines, the biocompatibility of the compositions of the present invention can be assessed using, for example, MSCs (mesenchymal stem cells from bone marrow), L929 (fibroblast like cells), and HUVEC (human umbilical vein endothelial cells). Further, to determine the potential of the silorane compositions to induce mineralization as another measure of its biocompatibility with bone, differentiation assays, such as alkaline-phosphatase, and mineralization assays, such as alizarin red and von Kossa staining, may be performed on the MLO-A5 cell line. These tests will determine the effect of the polymer on the ability of cells to proliferate, differentiate, and form mineralized matrix.

Small Animal (Rat) Model: Pull-out strength ex vivo: These studies will be conducted according to published methods which have been used as an in vivo model for implants.

Male Sprague-Dawley rats (approximately 6 months old) will be sacrificed and kept in −80° C. freezer. The femora will be excised. A 2 mm hole will be drilled into the intercondylar notch with a Dremel drill bit to penetrate the subchondral cortical bone and gain access to the femoral intramedullary canal. The marrow cavity will be disrupted by inserting a threaded hand drill proximally through the entire length of the diaphysis to approximately the level of the lesser trochanter. A guide implant will be placed into the ablated cavity to ensure that the canal will be an appropriate size to accommodate the definitive implant. The cavity will then be flushed with 10 mL of sterile saline for removal of loose marrow contents. Following irrigation, bone cement (chemically cured silorane and fillers (bone cement mimic) or commercial bone cement) will be introduced into the intramedullary canal with a root canal filler and then a titanium implant, 22 mm long and 1.5 mm diameter, will be implanted in a retrograde manner. The femora implanted with titanium rods fixed with bone cement mimic or commercial bone cement will be kept 24 hours and tested biomechanically. The 2-4 mm of distal rod (implant) will be exposed; proximal half of femur will be embedded in dental acrylic in a holder. The holder is a lower part of a 15 mL centrifuge tube which is cut at mark-line 3 mL and can be filled 3 g of dental acrylic and is attached an eye hook at bottom. The exposed implant will be gripped with a drill chuck and S hooks will be placed at lower end of the specimen to keep coaxial alignment of the implant with the direction of force. The pullout test will be conducted at a displacement rate of 0.25 mm/min to failure with the force (N). The values will be calculated by dividing the force at the point of failure by the surface area of the implant in the femur. This result will determine if the silorane based bone cement provides adequate mechanical support.

Osteointegration of the silorane bone cement in vivo: After ex vivo testing, the osseointegration with the silorane bone cement or PMMA bone cement will be assessed. The general biological response, including inflammation and bone mineralization, must also be characterized for the silorane bone cements. The samples will be split into two parts: pull-out strength and histological analysis.

Implant Placement: Male Sprague-Dawley rats (approximately 6 months old) will be placed under general anesthesia via isofluorane inhalation (3-4% for induction), ketamine/dex-medetomidine (75/0.5 mg/kg body weight; IP) for maintenance. The animal will be weighed and the both legs will be shaved with a standard clipper and disinfected with povidone/iodine solution. Animals will be placed on a warming pad during surgery as provided in the animal facility (recirculating water heating pad). All procedures will be performed under aseptic conditions. A 1 cm lateral parapatellar incision will be made to expose the knee joint. The patella will be retracted medially with the knee extended. The knee will be slowly flexed to expose the intercondylar notch. A 2 mm hole will be drilled into the intercondylar notch with a Dremel drill bit to penetrate the subchondral cortical bone and gain access to the femoral intramedullary canal. The marrow cavity will be disrupted by inserting a threaded hand drill proximally through the entire length of the diaphysis to approximately the level of the lesser trochanter. A guide implant will be placed into the ablated cavity to ensure that the canal will be an appropriate size to accommodate the definitive implant. The cavity will then be flushed with 10 mL of sterile saline for removal of loose marrow contents. Following irrigation, bone cement (chemically cured silorane and fillers or commercial bone cement) will be introduced into the intramedullary canal, and then a titanium implant, 22 mm long and 1.5 mm diameter, will be implanted in a retrograde manner. The capsule and skin will be sutured with 4-0 nylon. Buprenex, 0.01-0.05 mg/kg and Atipamezole, 0.1-1 mg/kg will be administered intraperitoneally to the rat immediately post operation. The animal will be allowed to fully recover in a separate cage on the warming pad and will be allowed activity ad libitum.

Post-op Analysis: The inflammatory response of incision and movement of operated limb will be monitored every day. Microcomputed tomography (MicroCT) and X-ray will be taken at weeks 1, 4, and 8 weeks post surgery. Animals will be euthanized by $CO_2$ asphyxiation at 1 (to examine for any inflammatory reaction) and 8 weeks (to examine for osseointegration) post surgery. The femurs for mechanical testing will be harvested, denuded of soft tissue, and frozen at −20° C. The procedure of mechanical test could be seen above. The femurs for histology will be placed in 10% neutral buffered formalin.

Tissue Preparation, Histology, and Histomorphometry: After placement and sacrifice, bones will be fixed in neutral buffered formalin, decalcified and embedded for frozen sections by standard techniques. Serial sections will be cut and stained with Hematoxylin and Eosin (H&E) or Goldner's trichrome using standard techniques. Staining for both TRAP and alkaline phosphatase can be performed. Undecalcified methacrylate embedded sections will also be stained by the von Kossa procedure as described previously for determination of the mineralized bone volume by histomorphometry.

Histomorphometric Analysis: Histomorphometric analysis will be performed on long bones using a Nikon E800 microscope with live video image capabilities that is interfaced with the Osteomeasure bone histomorphometry software. The parameters to be measured from H&E and/or Goldner's trichrome stained sections include trabecular and cortical bone volume, osteoid seam thickness, and osteoblast numbers per mm bone surface. TRAP stained sections will be used for determination of the number of osteoclasts per mm bone surface. Von Kossa stained sections will be used to measure the volume of mineralized bone which will be expressed as a percentage of the total bone volume (i.e., including osteoid). Three non-consecutive sections (100 μm apart) from each specimen will be used for the histomorphometric analyses described above and these measurements will be performed by an individual who is without knowledge of the sample identities. Values will be expressed as the mean±standard error. Examination for wear debris particles in the surrounding tissue will be performed.

All publications, patents, patent applications, databases, and other references cited in this application are herein incorporated by reference in their entirety as if each individual publication, patent, patent application, database, or other reference were specifically and individually indicated to be incorporated by reference.

Aoki, U.S. Pat. No. 6,255,428 for Preparation of Epoxy Group-Bearing Organopolysiloxane or Organosilane (2001)

Beyer et al., *Mesenchymal stem cells: isolation, in vitro expansion and characterization*, Handbook Exp Pharmacol 174 249-282 (2006)

Bonewald et al., *Staining alone is not sufficient to confirm that mineralizations in vitro represents bone formation*, Calcified Tissue International 72(5) 537-547 (2003)

Bonewald, *Mechanosensation and Transduction in Osteocytes*, BoneKey 3(10) 7-15 (2006)

Chappelow et al., *Photopolymerization of a Novel Tetraoxaspiroundecane and Silicon-Containing Oxiranes*, J Appl Polym Sci 103(1) 336-344 (2006)

Chappelow et al., *Photopolymerization of Stress-Reducing Tetraoxaspiro[5,5]undecanes in Silorane-Based Matrix Resins*, J Dent Res 85 (SI-A) Abstract No. 823 (2006)

Chappelow et al., U.S. Provisional Patent No. 60,721,806 (09-29-2005)

Cornell, *Experiments with mixtures: designs, models, and the analysis of mixture data*, New York Wiley xix 649 3rd ed. (2002)

Crivello et al., *The synthesis and cationic polymerization of multifunctional silicon-containing epoxy monomers and oligomers*, J Polym Sci Part A Polym Chem 32 683-697 (1994)

Dunne et al., *Curing characteristics of acrylic bone cement*, J Mater Sci Mater Med 13(1) 17-22 (2002)

Edgell et al., Permanent *cell line expressing human factor VIII-related antigen established by hybridization*, Proc Natl Acad Sci USA 80(12) 3734-3737 (1983)

Eick et al., *In vitro biocompatibility of oxirane/polyol dental composites with promising physical properties*, Dent Mater 18(5) 413-421 (2002)

Eick et al., *Physical Properties of Silorane-Based Matrix Resins Containing Stress-Reducing Monomers*, J Dent Res 85 (SI-A) Abstract No. 897 (2006)

Eick et al., *Stability of silorane dental monomers in aqueous systems*, J. Dent. 34(6) 405-410 (2006)

Eick et al., *Properties of silorane-based dental resins and composites containing a stress-reducing monomer*, Dent Mater 23(8) 1011-1017 (2007)

Eick et al., *Mineralization Potential of Silorane and BIS-GMA/TEGDEMA Resins*, 85th Int'l Assoc Dent Res Ann Mtg, Abstract No. 1393 (2007)

Eick et al., *Expandable monomer silicon analogs and siloranes: II. physical properties testing*, J Dent Res 84 Abstract No. 1467 (2005)

Feng, *Dentin matrix protein 1, a target molecule for Cbfa1 in bone, is a unique bone marker gene*, Journal of Bone and Mineral Research 17(10) 1822-1831 (2002)

Feng et al., *Loss of DMP1 Causes Rickets and Osteomalacia and Identifies a Role for Osteocytes in Mineral Metabolism*, Nature Genetic 38 1310-1315 (2006)

Giese et al., *Determining Polymerization Volume Change of Oxiranes and Methacrylates Using Mercury Dilatometry*, 229th ACS National Meeting: Abstracts of Papers: ANYL-265 (2005)

Gomoll et al., *Nanoparticulate fillers improve the mechanical strength of bone cement*, Acta Orthop 79(3) 421-427 (2008)

Guggenberger et al., *Exploring beyond methacrylates*, Am J Dent 13 82D-84D (2000)

Guida et al., *Biological response of human bone marrow mesenchymal stem cells to fluoride-modified titanium surfaces*, Clin Oral Implants Res 21(11) 1234-1241 (2010)

Holder et al., *Toward a Cohesive Theory of Polymerization Volume Change, 1: General Requirements and Oxiranes*, Macromol Th Simulat 14 117-124 (2005)

Holder et al., *Rational Design of Dental Materials Using Computational Chemistry*, Dent Mater 21(1) 47-55 (2005)

Holder et al., *An Application of QM-QSAR to Predict and Rationalize the Refractive Index of a Wide Variety of Simple Organic/Organosilican Molecules*, QSAR Combin Sci 25(4) 342-349 (2006)

Ilie et al., *Silorane-based dental composite: behavior and abilities*, Dent Mater J 25(3) 445-454 (2006)

Ilie et al., *Macro-, micro-and nano-mechanical investigations on silorane and methacrylate-based composites*, Dent Mater 25(6) 810-819 (2009)

ISO, *Implants for surgery—Acrylic resin cements*, Geneva, Switzerland (2002)

Kato et al., *Establishment of an osteoid preosteocyte-like cell MLO-A5 that spontaneously mineralizes in culture*, J Bone Miner Res 16(9) 1622-1633 (2001)

Kilway et al., *Molecular Assembly of 1,3,5-Tris(cyanomethyl) and 1,4-Bis(cyanomethyl) Arenes with Silver Triflate*, Pure Appl Chem 78(4) 855-871 (2006)

Kostoryz et al., *Effects of dental resins on TNF-alpha-induced ICAM-1 expression in endothelial cells*, J Dent Res 80(9) 1789-1792 (2001)

Kostoryz et al., *Assessment of Relative Skin Sensitization Potency of Dental Monomers*, J Biomed Mater Res 79(3) 684-688 (2006)

Kostoryz et al., *Cytotoxicity evaluation of silorane polymers in odontoblast like cells*, J. Dent. Res 85(A) Abstract#1654 (2006)

Kostoryz et al., *Assessment of cytotoxicity and DNA damage exhibited by siloranes and oxiranes in cultured mammalian cells*, Mutat Res 634(1-2) 156-162 (2007)

Kuehn et al., *Acrylic bone cements: mechanical and physical properties*, Orthop Clin North Am 36(1) 29-39 (2005)

Lamoreaux, U.S. Pat. No. 3,220,972 for Organosilicon Process Using a Chloroplatinic Acid Reaction Product as the Catalyst (1965)

Lane et al., *Glucocorticoid-Treated Mice Have Localized Changes in Trabecular Bone aterial Properties and Osteocyte Lacunar Size That Are Not Observed in Placebo-Treated or Estrogen-Deficient Mice*, J Bone Miner Res 21(3) 466-476 (2006)

Lewis, *Alternative acrylic bone cement formulations for cemented arthroplasties: present status, key issues, and future prospects*, Journal of Biomedical Materials Research Part B, Applied Biomaterials 84(2) 301-319 (2008)

Lien et al., *Physical properties of a new silorane-based restorative system*, Dent Mater 26(4) 337-344 (2010)

Miller et al., *A Theoretical Study of an Expanding Monomer and an Oxirane Part 2: Oxirane and Copolymer Reactions*, J Mol Struct THEOCHEM 756(1-3) 195-203 (2005)

Miller et al., *Matrix-Assisted Laser Desorption/Ionization Time-of-Flight Analysis of the Copolymerization Reaction of an Expanding Monomer with a Diepoxide*, J Polym Sci [A1] 43(23) 5962-5970 (2005)

Mosna et al., *Human Bone-Marrow And Adipose Tissue Mesenchymal Stem Cells*: A User's Guide, Stem Cells Dev.

Nalvarte-Kostoryz et al., *Biocompatibility of the silorane resin to develop biomaterials for temporary bone stabilization*, J. Biomed. Mater. Res. Part B Applied Biomaterials (in press).

Nicolella et al., *Osteocyte Lacunae Tissue Strain in Cortical Bone*, J Biomech 39(9) 1735-1743 (2006)

Piepel et al., *Mixture experiment approaches: examples, discussion, and recommendations*, J Qual Tech 26(3) 177-195 (1994)

Puska et al., *Flexural properties of crosslinked and oligomer-modified glass-fibre reinforced acrylic bone cement*, J Mater Sci Mater Med 15(9) 1037-1043 (2004)

Radev et al., *Potential for thermal damage to articular cartilage by PMMA reconstruction of a bone cavity following tumor excision: a finite element study*, J Biomech 42(8) 1120-1126 (2009)

Ries et al., *In vivo behavior of acrylic bone cement in total hip arthroplasty*, Biomaterials 27(2) 256-261 (2006)

Ritter et al., *Systemic effects of polymethylmethacrylate: increased serum levels of gamma-glutamyltranspeptidase following arthroplasty*, Acta Orthop Scand 55(4) 411-413 (1984)

Saha et al., *Mechanical properties of bone cement: a review*, J Biomed Mater Res 18(4) 435-462 (1984)

Sanford et al., *The growth in vitro of single isolated tissue cells*, J Natl Cancer Inst 9(3) 229-246 (1948)

Sena et al., *Effect of recombinant human transforming growth factor-beta2 dose on bone formation in rat femur titanium implant model*, J Biomed Mater Res A. 92(3) 1210-1217 (2010)

Sengun et al., *Cytotoxicity of Silorane-Based Composite in a Dentin Barrier Test*, J Dent Res 84(A) Abstract #0122 (2005)

Spencer et al., *Micro-Raman Spectroscopy: Principles and Applications in Dental Research*, Photonics in Dentistry, Editor Kishen, A (in press).

Wang et al., *Effect of Co-Initiator and Water on the Photoreactivity and Photopolymerization of HEMA/Camphoquinone-Based Reactant Mixtures*, J Biomed Mater Res 78 721-728 (2006)

Wang et al., *Comparison of Interfacial Characteristics of Adhesive Bonding to Superficial Versus Deep Dentin Using SEM and Staining Techniques*, J Dent 34 26-34 (2006)

Wang et al., *Micro-Raman Imaging Analysis of Monomer/Mineral Distribution in Intertubular Region of Adhesive/Dentin Interfaces*, J Biomed Opt 11:024005/1-024005/7 (2006)

Weimnann et al., *Siloranes in dental composites*, Dent Mater 21(1) 68-74 (2005)

Ye et al., *Relationship of Photopolymerization Processes, Structure and Properties in Dentin Adhesives*, J Biomed Mater Res A 80 342-350 (2006)

Zhang et al., *E11/Gp38 Selective Expression in Osteocytes: Regulation by Mechanical Strain and Role in Dendrite Elongation*, Mol Cell Biol 26(12) 4539-4552 (2006)

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying figures are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. A biomaterial composition comprising:
a polymerizable silorane monomer, and
a curing system selected from the group consisting of a chemical curing system and a dual chemical/light curing system,
wherein the curing system comprises a rhodium-based or platinum-based organometallic catalyst, and wherein said silorane monomer comprises a mixture of 2,4,6,8-tetramethyl-2,4,6,8-tetrakis-[2-(7-oxabicyclo[4.1.0]hept-3-yl)ethyl]-1,3,5,7-tetraoxa-2,4,6,8-tetrasilacyclooxtane (CYGEP) and methylbis[2-(7-oxabicyclo[4.1.0]hept-3-yl)ethyl]phenylsilane (PHEPSI).

2. The biomaterial composition of claim 1 wherein said curing system comprises an organometallic catalyst selected from the group consisting of Lamoreaux's catalyst, Wilkinson's catalysts, Speier's catalyst, and Karstedt's catalyst, or mixtures thereof.

3. The biomaterial composition of claim 1 wherein said chemical curing system further comprises a photoacid.

4. The biomaterial composition of claim 3, wherein said photoacid is a phenyliodonium compound.

5. The biomaterial composition of claim 4 wherein said photoacid is selected from the group consisting of (4-n-octyloxyphenyl)phenyliodonium hexafluoroantimonate, [4-(2-hydroxy-tetradecyloxyphenyl)]phenyliodonium hexafluoroantimonate, [4-1-methylethyl)-phenyl](4-methylphenyl)iodonium tetrakis(pentafluorophenyl)borate(1-), and combinations thereof.

6. The biomaterial composition of claim 1 wherein said curing system is a dual chemical/light curing system, wherein said dual chemical/light curing system additionally comprises an acid selected from the group consisting of a Bronsted acid, Lewis acid, and a superacid, and mixtures thereof.

7. The biomaterial composition of claim 1 wherein said curing system is a dual chemical/light curing system additionally comprises an acid selected from the group consisting of acetic acid, phosphoric acid, sulfuric acid, hydrobromic acid, hydroiodic acid, trichloroacetic acid, trifluoroacetic acid, p-toluenesulfonic acid, boron trifluoride, aluminium chloride, tin (IV) chloride, titanium chloride, pentafluoroproprionic acid, triflic acid, hexafluorophosphoric acid, ethyl triflate, potassium t-butoxide, and mixtures thereof.

8. The biomaterial composition of claim 7 wherein said dual chemical/light curing system further comprises a photosensitizer.

9. The biomaterial composition of claim 8 wherein said photosensitizer is a diketone.

10. The biomaterial composition of claim 7 wherein said dual chemical/light curing system further comprises an electron donor compound in which said electron donor is a substituted amine.

11. The biomaterial composition of claim 7 wherein said dual chemical/light curing system comprises acetic acid, p-(octyloxyphenyl)phenyliodonium hexafluoroantimonate, and camphorquinone.

12. The biomaterial composition of claim 11 further comprising a filler.

13. The biomaterial composition of claim 12 further comprising a tetraoxaspiro[5.5]undecane.

14. The biomaterial composition of claim 1 wherein said curing system is a dual chemical/light curing system, wherein said dual chemical/light curing system comprises a rhodium or platinum-based organometallic catalyst and a light initiation system having a photoacid, photosensitizer, and an electron donor.

15. The biomaterial composition of claim 14 wherein
said organometallic catalyst is selected from the group consisting of Lamoreaux's catalyst, Wilkinson's catalysts, Speier's catalyst, and Karstedt's catalyst;
said photoacid is a phenyliodonium compound;
said photosensitizer is a diketone; and
said electron donor is a substituted amine.

16. The biomaterial composition of claim 14 wherein
said organometallic catalyst comprises Lamoreaux's catalyst;
said photoacid comprises p-(octyloxyphenyl)phenyliodonium hexafluoroantimonate;
said photosensitizer comprises camphorquinone; and
said electron donor comprises ethyl p-dimethylaminobenzoate.

17. The biomaterial composition of claim 16 further comprising a filler.

18. The biomaterial composition of claim 17 further comprising a tetraoxaspiro[5.5]undecane.

19. The biomaterial composition of claim 1 further comprising one or more tetraoxaspiro[5.5]undecanes.

20. The biomaterial composition of claim 19, wherein said tetraoxaspiro[5.5]undecane is selected from the group consisting of a 2,4,8,10-tetraoxaspiro[5.5]undecane or a 1,5,7,11-tetraoxaspiro[5.5]undecane.

21. The biomaterial composition of claim 19 wherein said tetraoxaspiro[5.5]undecane is selected from Formulas A1 and A2

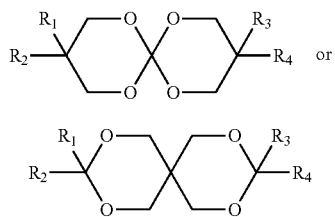

wherein $R_1$ and $R_3$ are independently is alkyl, aryl, aralkyl, or hydrogen; and wherein $R_2$ and $R_4$ are independently alkenoxy, alkenoxyalkyl, or silicon-containing moiety selected from alkylsilyl, arylsilyl, arylalkylsilyl, alloxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy.

22. The biomaterial composition of claim 19, wherein said tetraoxaspiro[5.5]undecane is selected from the group consisting of 3,9-diethyl-3,9-bis(allyloxymethyl)-1,5,7,11-tetraoxaspiro[5.5]undecane (DEBAOM-1,5,7,11-TOSU); 3,9-bis(3-trimethylsilylpropyl)-1,5,7,11-tetraoxaspiro[5.5]undecane (BTMSP-1,5,7,11-TOSU); 3,9-bis(allyloxymethyl)-2,4,8,10-tetraoxaspiro[5.5]undecane (BAOM-2,4,8,10-TOSU); 3,9-bis(2-trimethylsilylethyl)-2,3,8,10-tetraoxaspiro[5.5]undecane (BTMSE-2,4,8,10-TOSU); 5,5-diethyl-19-oxadispiro[1,3-dioxane-2,2'-1,3-dioxane-5',4''-bicyclo[4.1.0]heptane ](DECHE-1,5,7,11-TOSU); 3,9-diethyl-3,9-bis(3-trimethylsilylpropyloxymethyl)-1,5,7,11-tetraoxaspiro[5.5]-undecane (DEBTMSPOM-1,5,7,11-TOSU); (9-allyloxymethyl-9-ethyl-1,5,7,11-tetraoxaspero[5.5]undec-3-ylmethyl)-dimethylphenyl-silane (AOME-TOSU-MDMPS); and methyl[2-(7-oxabicyclo[4.1.0]hept-3-yl)ethyl]-pheynl[3-(3,9,9-triethyl-1,5,7,11-tetraoxaspiro[5.5]undec-3-ylmethoxy)propyl]silane (MOB-HEP-TETOSU-MOPS).

23. The biomaterial composition of claim 1 further comprising a filler.

24. The biomaterial composition of claim 1 further comprising a pre-polymerized polymer derived from said polymerizable silorane monomer.

25. The biomaterial composition of claim 1 comprising about 30 to 60 wt % silorane monomers; about 1 to 50 wt % of a pre-polymerized polymer derived from the silorane monomers; and about 0.05 to 5 wt % of the chemical curing system or dual chemical/light curing system, and wherein said curing system comprises acetic acid or Lamoreaux's catalyst.

26. The biomaterial composition of claim 25 further comprising about 5 to 50 wt % of a filler.

27. The biomaterial composition of claim 1 wherein said composition after polymerization exhibits a peak exotherm below about 30° C.

28. The biomaterial composition of claim 1 wherein said composition after polymerization exhibits a flexural strength of about 22 to 50 MPa.

29. The biomaterial composition of claim 1 wherein said composition after polymerization exhibits a flexural modulus about 1.5 to 3.5 GPa.

30. The biomaterial composition of claim 1 further comprising a heat-sensitive antimicrobial or growth factor that is stable at about 25 to 30° C.

31. The biomaterial composition of claim 1 further comprising a growth factor selected from the group consisting of TGFβ1, TGFβ2, TGFβ3, BMP-2, BMP-3, BMP-4, BMP-5, BMP-6, BMP-7, BMP-8, BMP-9, CDMP-1, CDMP-2, or CDMP-3.

* * * * *